US010415962B2

(12) United States Patent
Chang et al.

(10) Patent No.: US 10,415,962 B2
(45) Date of Patent: Sep. 17, 2019

(54) NON-CONTACT AND OPTICAL MEASURING AUTOMATION SYSTEM FOR THE PROFILE ACCURACY OF DISK CAMS AND METHOD THEREOF

(71) Applicant: National Taiwan Ocean University, Keelung (TW)

(72) Inventors: Wen-Tung Chang, Taipei (TW); Chun-Cheng Lu, New Taipei (TW); Hsiang-Lun Kao, New Taipei (TW)

(73) Assignee: National Taiwan Ocean University, Keelung (TW)

( * ) Notice: Subject to any disclaimer, the term of this patent is extended or adjusted under 35 U.S.C. 154(b) by 177 days.

(21) Appl. No.: 15/824,798

(22) Filed: Nov. 28, 2017

(65) Prior Publication Data

US 2019/0063908 A1 Feb. 28, 2019

(30) Foreign Application Priority Data

Aug. 25, 2017 (TW) .............................. 106129071 A

(51) Int. Cl.

| *G01B 11/26* | (2006.01) |
|---|---|
| *G01B 11/24* | (2006.01) |
| *F16H 53/00* | (2006.01) |
| *G01N 21/89* | (2006.01) |
| G01N 21/47 | (2006.01) |
| G01B 11/06 | (2006.01) |

(52) U.S. Cl.
CPC ............. *G01B 11/26* (2013.01); *F16H 53/00* (2013.01); *G01B 11/24* (2013.01); *G01N 21/8901* (2013.01); *G01B 11/0608* (2013.01); *G01N 21/4788* (2013.01); *G01N 2021/479* (2013.01)

(58) Field of Classification Search
CPC ..... F16H 53/00; G01B 11/26; G01B 11/0608; G01B 11/24
See application file for complete search history.

(56) References Cited

U.S. PATENT DOCUMENTS

| 5,145,022 | A | * | 9/1992 | Kido | ..................... | B62D 7/1581 |
|---|---|---|---|---|---|---|
| | | | | | | 180/412 |
| 10,151,585 | B1 | * | 12/2018 | Chang | .................. | G01B 11/303 |
| 2003/0140509 | A1 | * | 7/2003 | Casagrande | ............. | B61K 9/08 |
| | | | | | | 33/287 |
| 2012/0242827 | A1 | * | 9/2012 | Chang | ..................... | G01B 11/08 |
| | | | | | | 348/92 |
| 2016/0187121 | A1 | * | 6/2016 | Chang | ................ | G01B 11/2433 |
| | | | | | | 356/630 |

* cited by examiner

*Primary Examiner* — Violeta A Prieto
(74) *Attorney, Agent, or Firm* — Huffman Law Group, PC

(57) ABSTRACT

A non-contact and optical measuring automation system, configured to electrically connect to a computer to measure the profile accuracy of a disk cam, includes a base, a rotating chuck, a moving stage module and a laser displacement meter. The rotating chuck is disposed for clamping the disk cam. The moving stage module includes a first linear motion stage movable relative to the base in a first direction and a second linear motion stage movable relative to the first linear motion stage in a second direction. The computer is able to control the rotation of the rotating chuck and the movement of the moving stage module, and is able to control a beam emitted from the laser displacement meter projecting onto a profile surface of the disk cam so as to obtain a profile deviation value of the disk cam by using the laser triangulation method.

10 Claims, 18 Drawing Sheets

NON-CONTACT AND OPTICAL MEASURING AUTOMATION SYSTEM FOR THE PROFILE ACCURACY OF DISK CAMS AND METHOD THEREOF

CROSS-REFERENCE TO RELATED APPLICATIONS

This non-provisional application claims priority under 35 U.S.C. § 119(a) on Patent Application No(s). 106129071 filed in Taiwan, R.O.C. on Aug. 25, 2017, the entire contents of which are hereby incorporated by reference.

BACKGROUND

Technical Field

This disclosure relates to a measuring automation system and measuring method for the profile accuracy of a disk cam, and particularly to an optical measuring automation system and measuring method for measuring the profile accuracy in a non-contact manner.

Related Art

Cams are mechanical components commonly used in various machines and automation equipment. The cam makes its follower to produce a prescribed motion through direct contact in order to achieve required motion control. Generally, a disk cam is machined by using computer numerical control (CNC) machines to cut and grind its cam shape in order to obtain an accurate cam profile. When the manufacturing error of the cam profile exceeds its allowable tolerance, the positioning accuracy of the follower, in contact with the cam, will be influenced by the cam and thus deviates from its prescribed position. Furthermore, the dynamic performance of the cam mechanism will also be influenced so as to produce excessive vibration and noise in high-speed operations. Therefore, after the manufacturing processes for the disk cam, the profile accuracy of the disk cam must be inspected for quality control.

The measuring devices and methods for the profile accuracy of the cam are classified into two types including the contact type and the non-contact type. However, regarding the contact measuring devices and methods (e.g. conventional coordinate measuring machine and camshaft tester), a specialized probe or anvil has to contact the cam profile to be measured. The probe or anvil of the measuring device may slightly deform due to the force acting in contact with the measured cam profile, and such a situation may result in slight measuring error as well as the wear of the probe or the anvil.

Regarding the conventional non-contact measuring device and method, a laser scanner (also known as a scanning laser device) or an optical micrometer (also known as a linear array measuring device) may be applied. The laser scanner or the optical micrometer emits a parallel light beam surrounding the disk cam along the radial direction of the disk cam to form an optical measuring plane, and detects the range of the parallel light beam being blocked by the disk cam so as to obtain the profile deviation of the disk cam. A non-contact measuring method may prevent the deformation and the wear of the measuring device, and its measuring speed is higher than that of a contact measuring method. However, the conventional measuring device and method can be applied to a disk cam with a geometric feature of convex profile but cannot be applied to a disk cam with a geometric feature of concave profile. More specifically, when the concave profile of the disk cam rotates to an angular position for being measured, the parallel light beam emitted from the measuring device cannot project onto the hollow part of the concave profile, so that the profile deviation of the hollow part cannot be measured.

SUMMARY

According to one or more embodiments of this disclosure, a non-contact and optical measuring automation system is configured to electrically connect to a computer to measure the profile accuracy of a disk cam. The non-contact and optical measuring automation system comprises a base, a rotating chuck, a moving stage module and a laser displacement meter. The rotating chuck is disposed on the base and configured to clamp the disk cam to allow the disk cam to rotate around a rotational axis of the disk cam. The moving stage module comprises a first linear motion stage and a second linear motion stage. The first linear motion stage is disposed on the base and movable relatively to the base in a first direction, and the second linear motion stage is disposed on the first linear motion stage and movable relatively to the first linear motion stage in a second direction non-parallel to the first direction so as to be close to or far from the disk cam. The laser displacement meter is disposed on the second linear motion stage, and the second linear motion stage is configured to carry the laser displacement meter to move together in the second direction. The computer is configured to instruct the rotating chuck to carry the disk cam to rotate, and is configured to instruct the moving stage module to carry the laser displacement meter to move. The computer is further configured to instruct a light beam emitted from the laser displacement meter to project onto the actual profile point and then to obtain an actual distance between the actual profile point of the disk cam and the laser displacement meter by a laser triangulation method. Theoretical profile information of the disk cam comprises a theoretical profile point corresponding to the actual profile point, and a theoretical distance between the theoretical profile point and the laser displacement meter is defined. The computer obtains a profile deviation value of the disk cam corresponding to the theoretical profile point according to a difference value between the actual distance and the theoretical distance.

According to one or more embodiments of this disclosure, a non-contact and optical measuring method comprises steps as follows: inputting theoretical profile information of the disk cam; setting a measuring parameter, with the measuring parameter comprising at least one theoretical profile point of the theoretical profile information, with a theoretical distance defined between the at least one theoretical profile point and a laser displacement meter, and with the at least one theoretical profile point corresponding to at least one actual profile point of a profile surface of the disk cam; and executing a measuring procedure by the laser displacement meter, making a light beam emitted from the laser displacement meter project onto the at least one actual profile point so as to obtain an actual distance of the at least one actual profile point of the disk cam by a laser triangulation method, and obtaining a profile deviation value of the disk cam corresponding to the at least one theoretical profile point according to a difference value between the theoretical distance and the actual distance.

BRIEF DESCRIPTION OF THE DRAWINGS

The present disclosure will become more fully understood from the detailed description given herein below and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1A:
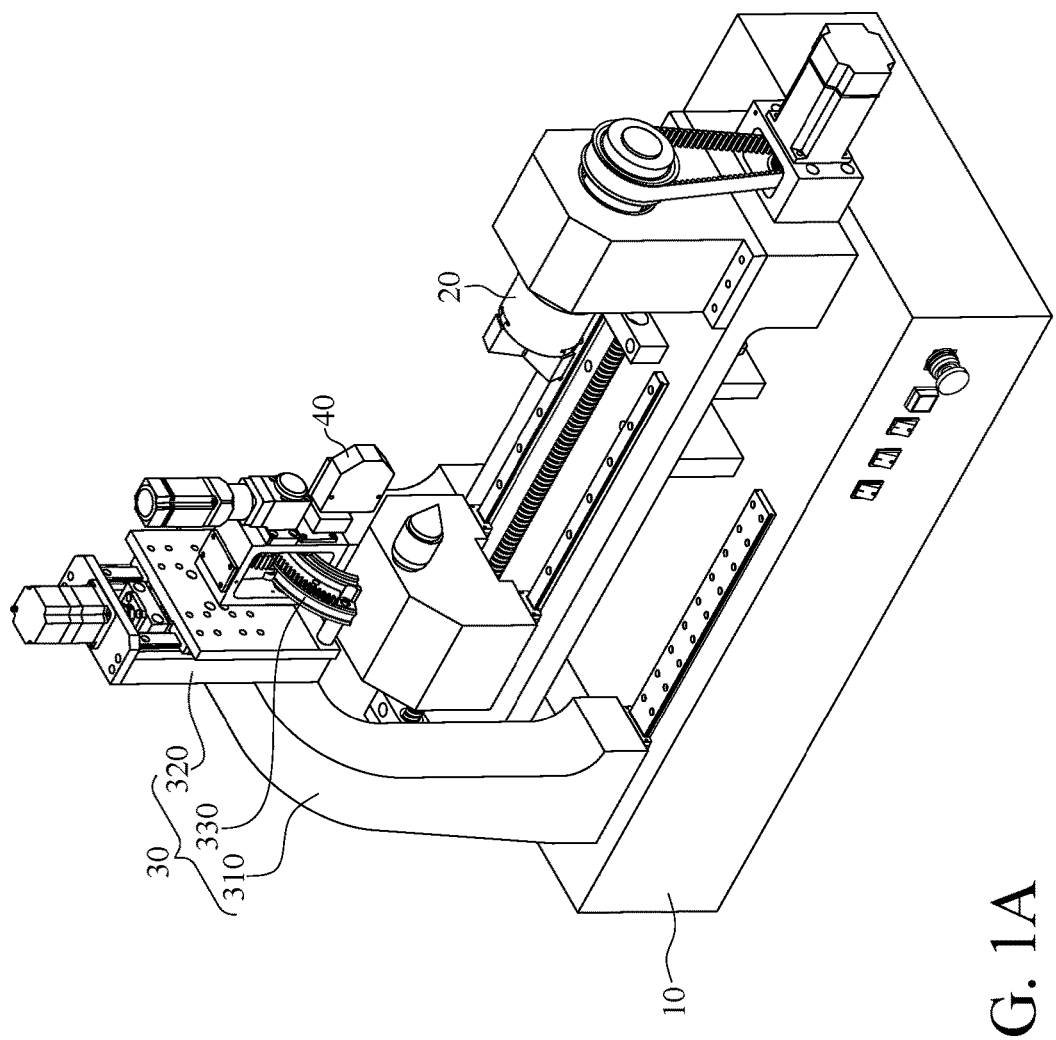
FIG. 1A is a perspective view of a non-contact and optical measuring automation system according to the first embodiment of this disclosure.
Figure 1B:
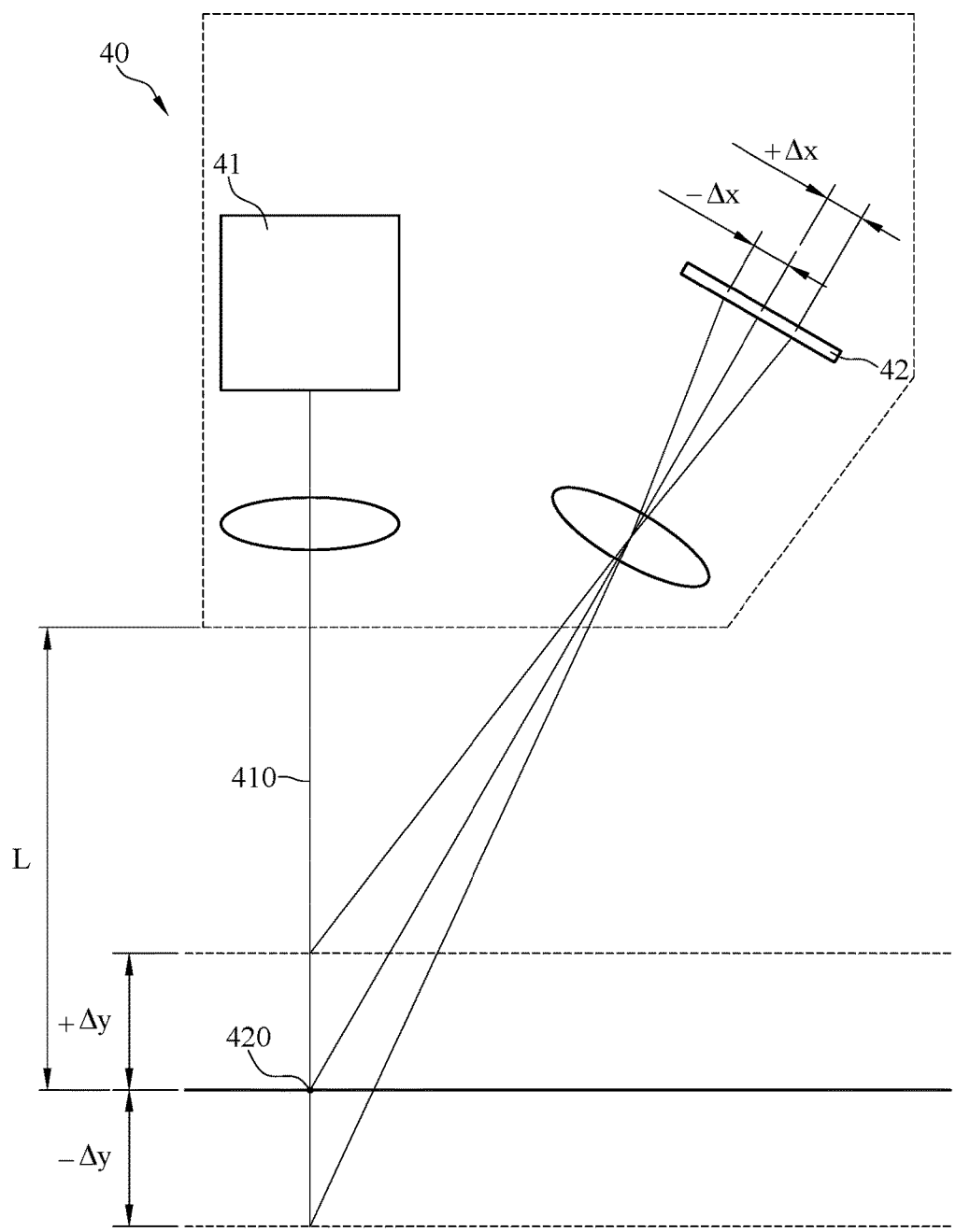
FIG. 1B is a schematic diagram of a laser triangulation method.
Figure 1C:
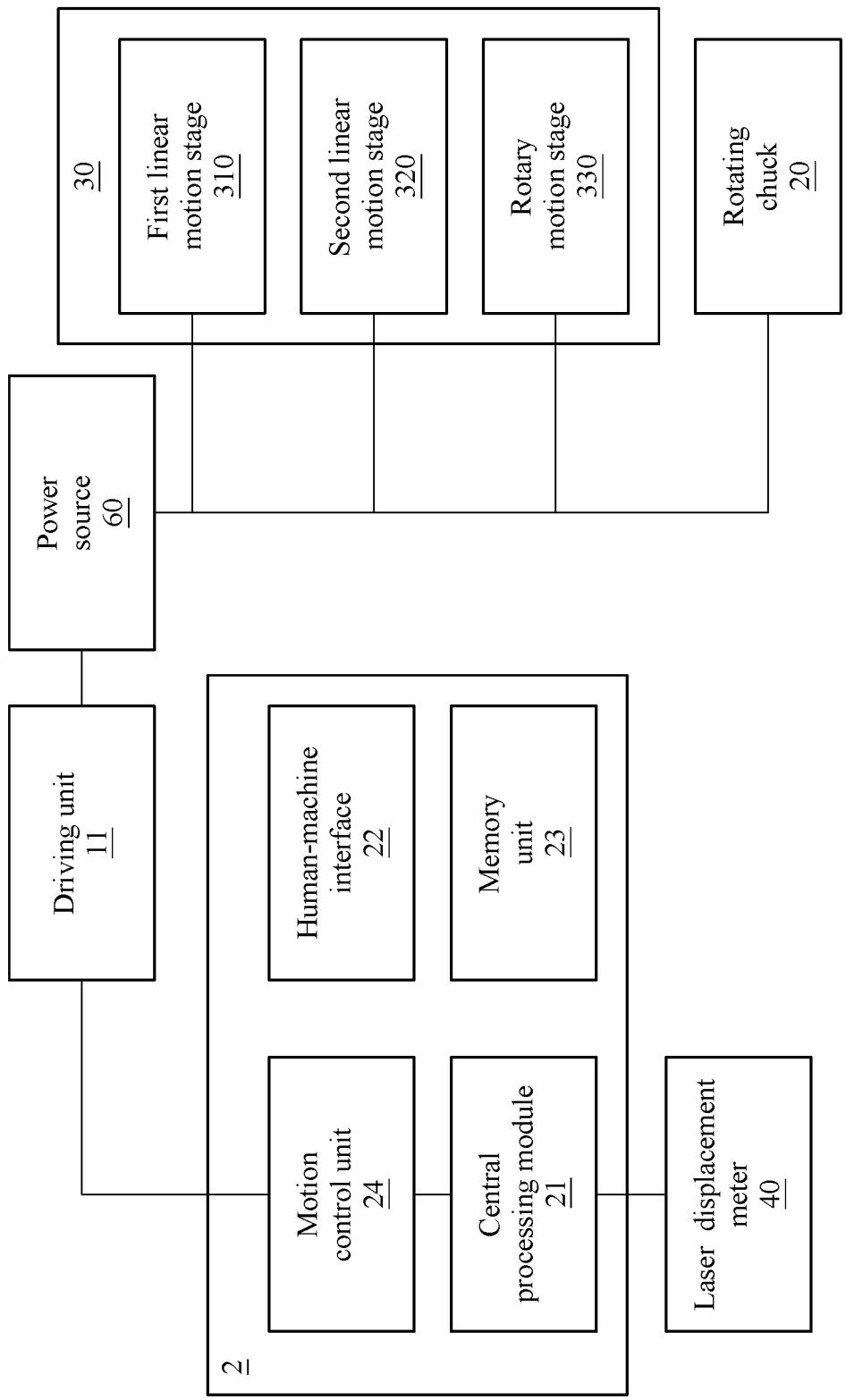
FIG. 1C is a block diagram of the non-contact and optical measuring automation system in FIG. 1A and a computer.
Figure 2:
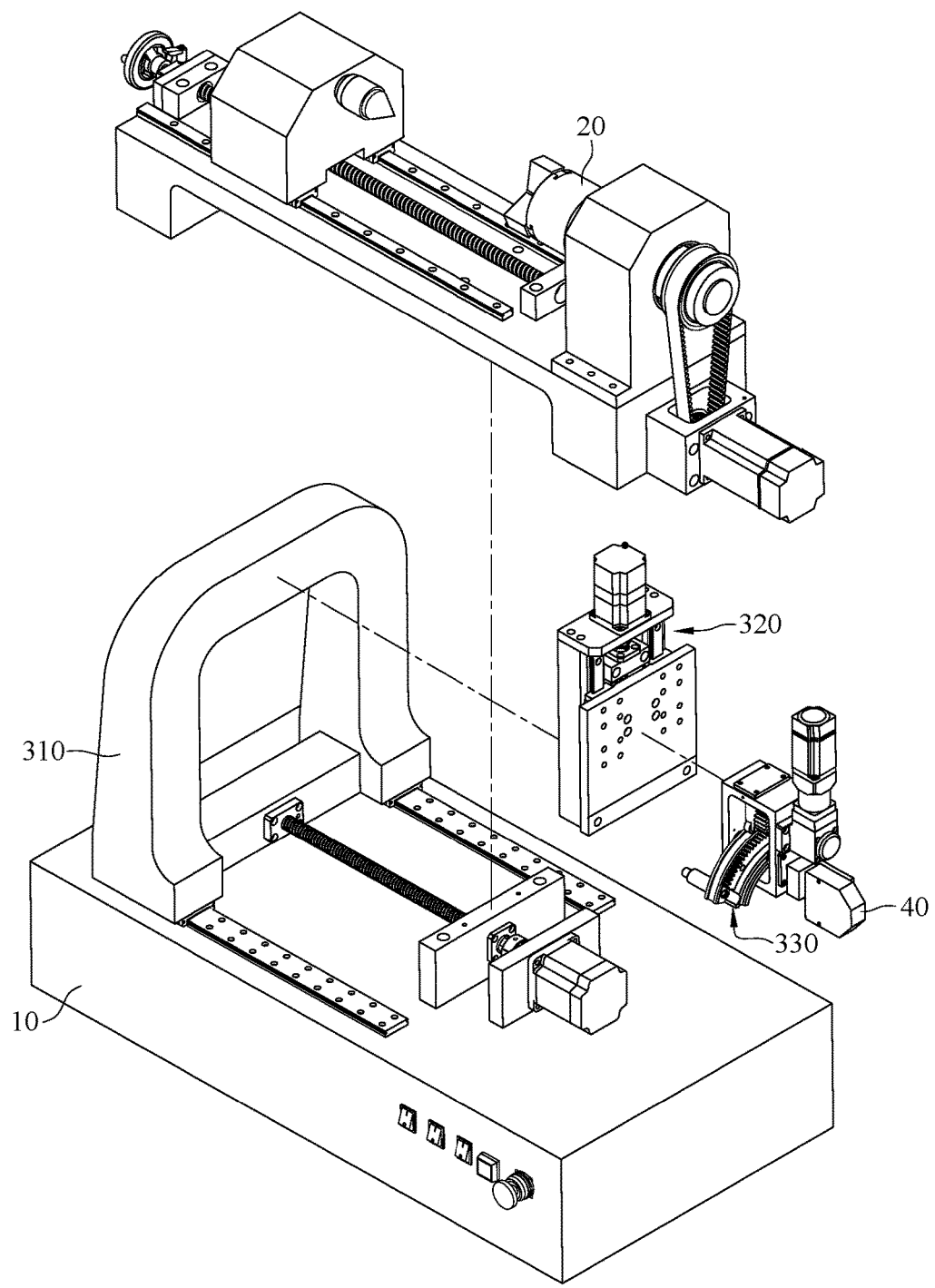
FIG. 2 is an exploded view of the non-contact and optical measuring automation system in FIG. 1A.
Figure 3A:
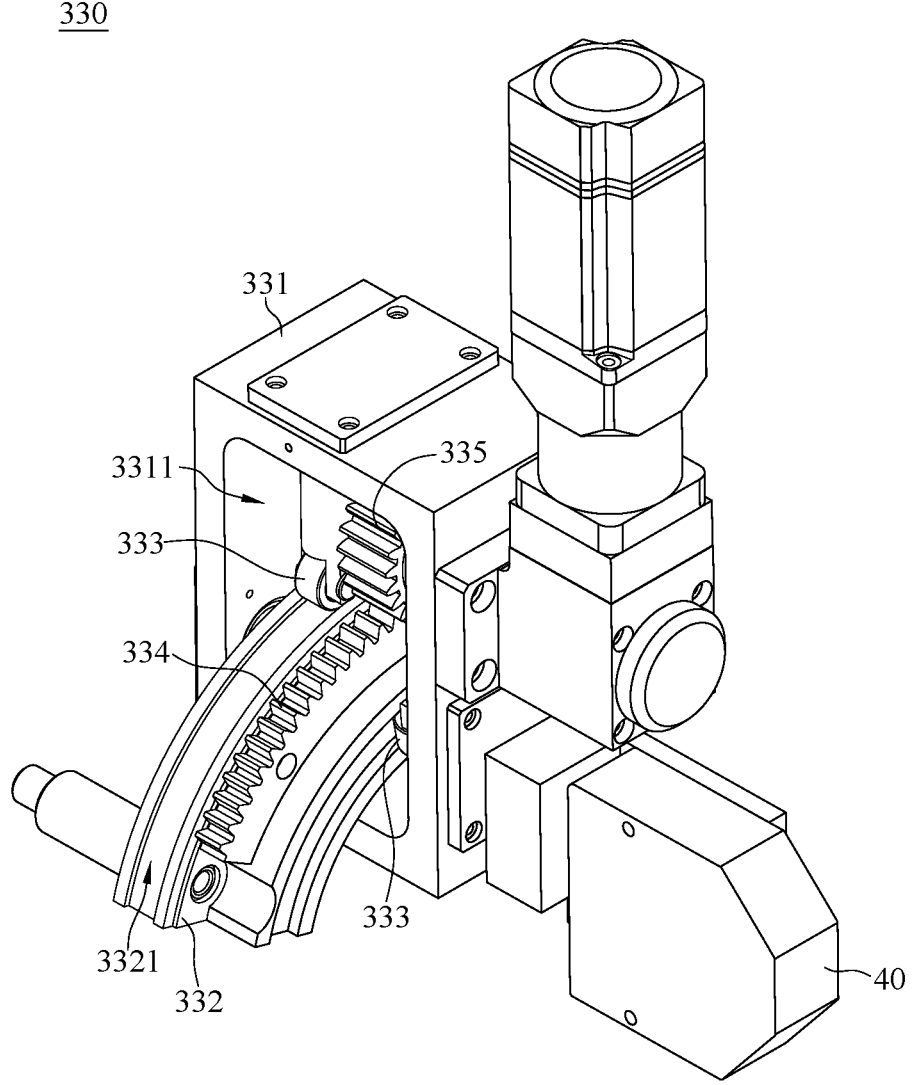
FIG. 3A is a perspective view of the rotary motion stage of the moving stage module in FIG. 2.
Figure 3B:
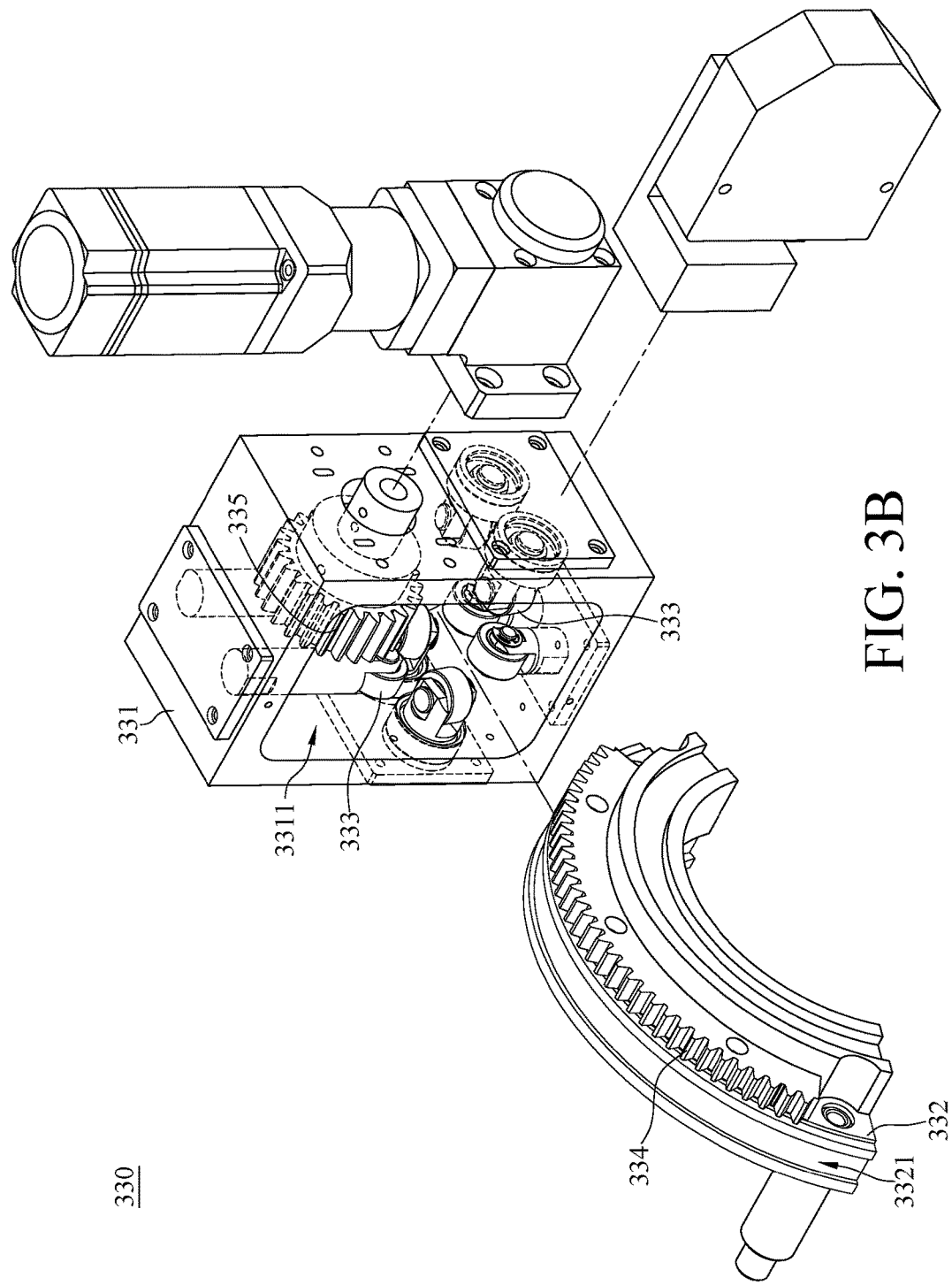
FIG. 3B is a an exploded view of the rotary motion stage in FIG. 3A.

Please refer to FIG. 1A to FIG. 3B. FIG. 1A is a perspective view of a non-contact and optical measuring automation system according to the first embodiment of this disclosure. FIG. 1B is a schematic diagram of a laser triangulation method. FIG. 1C is a block diagram of the non-contact and optical measuring automation system in FIG. 1A and a computer. FIG. 2 is a schematic breakdown drawing of the non-contact and optical measuring automation system in FIG. 1A. FIG. 3A is a perspective view of the rotary motion stage of the moving stage module in FIG. 2. FIG. 3B is an exploded view of the rotary motion stage in FIG. 3A. This embodiment provides a non-contact and optical measuring automation system 1 which measures the profile accuracy of a disk cam by an automatic and non-contact method. The non-contact and optical measuring automation system 1 includes a base 10, a rotating chuck 20, a moving stage module 30 and a laser displacement meter 40.

The rotating chuck 20 is disposed on the base 10 and is configured to clamp the disk cam to carry the disk cam to rotate around a rotational axis of itself. The function of the rotating chuck 20 will be further described hereafter.

The moving stage module 30 includes a first linear motion stage 310, a second linear motion stage 320 and a rotary motion stage 330. The first linear motion stage 310, the second linear motion stage 320 and the rotary motion stage 330 are respectively connected to a power source 60. The first linear motion stage 310 is disposed on the base 10, and can move relatively to the base 10 in a first direction D1. The second linear motion stage 320 is disposed on the first linear motion stage 310, and the second linear motion stage 320 can move relatively to the first linear motion stage 310 in a second direction D2 which is not parallel to the first direction D1. In this embodiment, the second direction D2 is perpendicular to the first direction D1.

The rotary motion stage 330 is rotatably disposed on the second linear motion stage 320. More specifically, the rotary motion stage 330 includes a rotary carriage 331, a circular rail member 332, a plurality of rollers 333, a segmented spur gear 334 and a pinion gear 335. The circular rail member 332 is disposed on the second linear motion stage 320 and passes through a through slot 3311 of the rotary carriage 331, and the circular rail member 332 has a plurality of bearing surfaces 3321 corresponding to these rollers 333. The rollers 333 are rotatably disposed in the through slot 3311, and these rollers 333 respectively contact with these bearing surfaces 3321, so that the rotary carriage 331 has rotatability relative to the circular rail member 332. The segmented spur gear 334 is fixed at the circular rail member 332, the pinion gear 335 is disposed on the shaft of the power source 60, the power source 60 is disposed at the rotary carriage 331, and the segmented spur gear 334 and the pinion gear 335 engage with each other, so that the relative motion between the segmented spur gear 334, the pinion gear 335 and the rotary carriage 331 are equivalent to a conventional planetary gear train. When the power source 60 is turned on, the rolling motion of the pinion gear 335 relative to the segmented spur gear 334 simultaneously carries the rotary carriage 331 to rotate relatively to the circular rail member 332, so as to allow the rotary motion stage 330 to rotate relatively to the second linear motion stage 320. In this embodiment, the rotary motion stage 330 can rotate relatively to the second linear motion stage 320 so as to have a radial measuring position and a normal measuring position, and the related details will be described later.

The laser displacement meter 40 is disposed on the rotary carriage 331 of the rotary motion stage 330, and the second linear motion stage 320 can move in the second direction D2 together with the rotary motion stage 330 and the laser displacement meter 40. In this embodiment, the laser displacement meter 40 includes a laser diode 41 and an electronic photo-sensing component 42. For example, the electronic photo-sensing component 42 is a complementary metal-oxide-semiconductor (CMOS) or a charge-coupled device (CCD). The laser diode 41 can emit a laser beam, and the electronic photo-sensing component 42 can receive and sense the scattering light which is generated when the laser projects onto an object to be measured.

When the object is located in the measuring range of the laser displacement meter 40, the laser beam emitted by the laser diode 41 serves as a light beam that projects onto the surface of the object so as to generate the scattering light, and a part of the scattering light projects onto the electronic photo-sensing component 42. The distance between the surface to be measured and the laser displacement meter 40 can be obtained by detecting the position where the scattering light projects onto on the electronic photo-sensing component 42. When the position of the surface to be measured changes, the position where the electronic photo-sensing component 42 receives the scattering light changes correspondingly. Thereby, the change in the distance between the surface to be measured and the laser displacement meter 40 can be estimated. Further, the measurement of the laser displacement meter 40 is executed by a laser triangulation method. As shown in FIG. 1B, when the laser beam emitted by the laser diode 41 is focused by a lens to generate a light beam 410 and projects onto the surface to be measured, the laser beam is scattered to generate the scattering light, and then the scattering light is focused by the lens and is projected onto the electronic photo-sensing component 42 to form a light spot. When the surface to be measured has a displacement quantity of $+\Delta y$ or $-\Delta y$ in a vertical direction, the light spot has the corresponding shift quantity of $+\Delta x$ or $-\Delta x$ on the surface of the electronic photo-sensing component 42, wherein $+\Delta y$ is proportional to $+\Delta x$ and $-\Delta y$ is proportional to $-\Delta x$. Therefore, the displacement quantity of $+\Delta y$ or $-\Delta y$ of the surface to be measured can be obtained according to the shift quantity of $+\Delta x$ or $-\Delta x$ of the light spot of the laser beam on the electronic photo-sensing component 42. When the displacement quantities of $+\Delta y$ and $-\Delta y$ are both zero, the measuring datum point 420 of the laser displacement meter 40 overlaps the surface to be measured, and at the same time, there is a theoretical distance L between the laser displacement meter 40 and the surface to be measured.

As shown in FIG. 1C, the rotating chuck 20, the moving stage module 30 and the laser displacement meter 40 of the non-contact and optical measuring automation system 1 can be electrically connected to a computer 2. More specifically, the computer 2 is an electronic device with a function of data processing, such as a desktop computer. The computer 2 includes a central processing module 21, a human-machine interface 22, a memory unit 23 and a motion control unit 24, and there is a driving unit 11 disposed in the base 10. The central processing module 21 of the computer 2 can be electrically connected to the driving unit 11 in the base 10, via the motion control unit 24 installed in the computer 2, and so as to instruct one or more power sources 60 drive the rotating chuck 20 to clamp and rotate the disk cam, drive the first linear motion stage 310 of the moving stage module 30 to move relatively to the base 10, drive the second linear motion stage 320 to move relatively to the first linear motion stage 310, and drive the rotary motion stage 330 to rotate relatively to the second linear motion stage 320. In this embodiment, stepping motors are selected as the power sources of the first linear motion stage 310 and the second linear motion stage 320, and servo motors are selected as the power sources of the rotating chuck 20 and the rotary motion stage 330. Moreover, linear encoders are respectively installed in the first linear motion stage 310 and the second linear motion stage 320, and rotary encoders are respectively installed in the servo motors of the rotating chuck 20 and the rotary motion stage 330. The linear encoders can respectively detect the moving positions of the first linear motion stage 310 and the second linear motion stage 320, and return the moving positions to the motion control unit 24 so as to execute a closed-loop motion control thereof. Besides, the rotary encoders can respectively detect the rotating angles of the rotating chuck 20 and the rotary motion stage 330, and return the rotating angles to the motion control unit 24 so as to execute the closed-loop motion control thereof. Thereby, the positioning accuracy, which is needed during the measurement, is achieved by the non-contact and optical measuring automation system 1.

The central processing module 21 can receive the displacement quantity of $+\Delta y$ or $-\Delta y$ via a communication interface (e.g. RS-232 interface), with the displacement quantity detected by the laser displacement meter 40. A user can input various measuring parameters, such as the type of the disk cam, profile point, cross-section to be measured etc., via the human-machine interface 22. On the other hand, the user can also monitor the operation of the measuring procedure or the various results measured during the measurement via the human-machine interface 22. The memory unit 23 can be configured to store the measuring parameters and the measuring results.

Figure 4A:
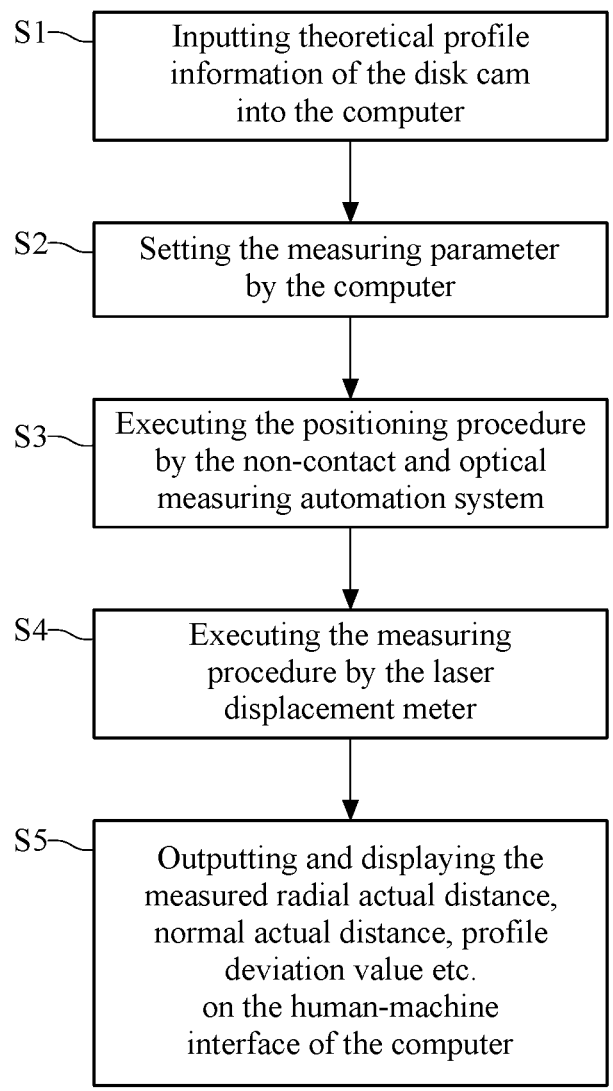
FIG. 4A is a flowchart of a non-contact and optical measuring method according to the first embodiment of this disclosure.
Figure 4B:
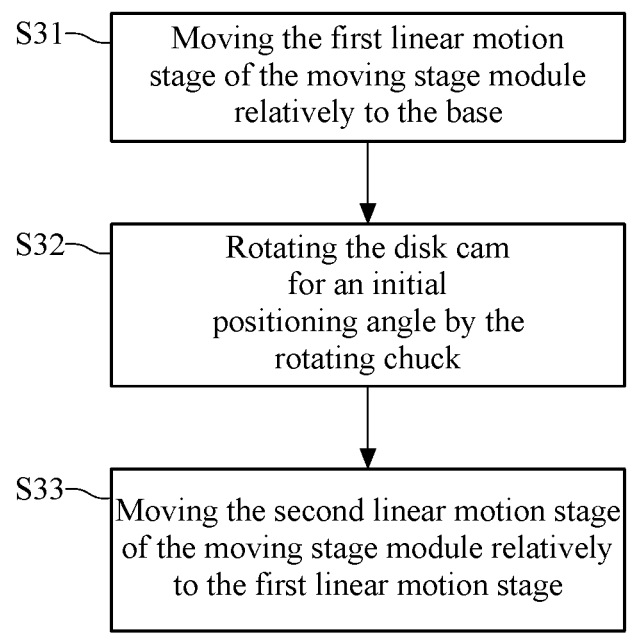
FIG. 4B is a flowchart of the positioning procedure of the optical measuring method in FIG. 4A.
Figure 4C:
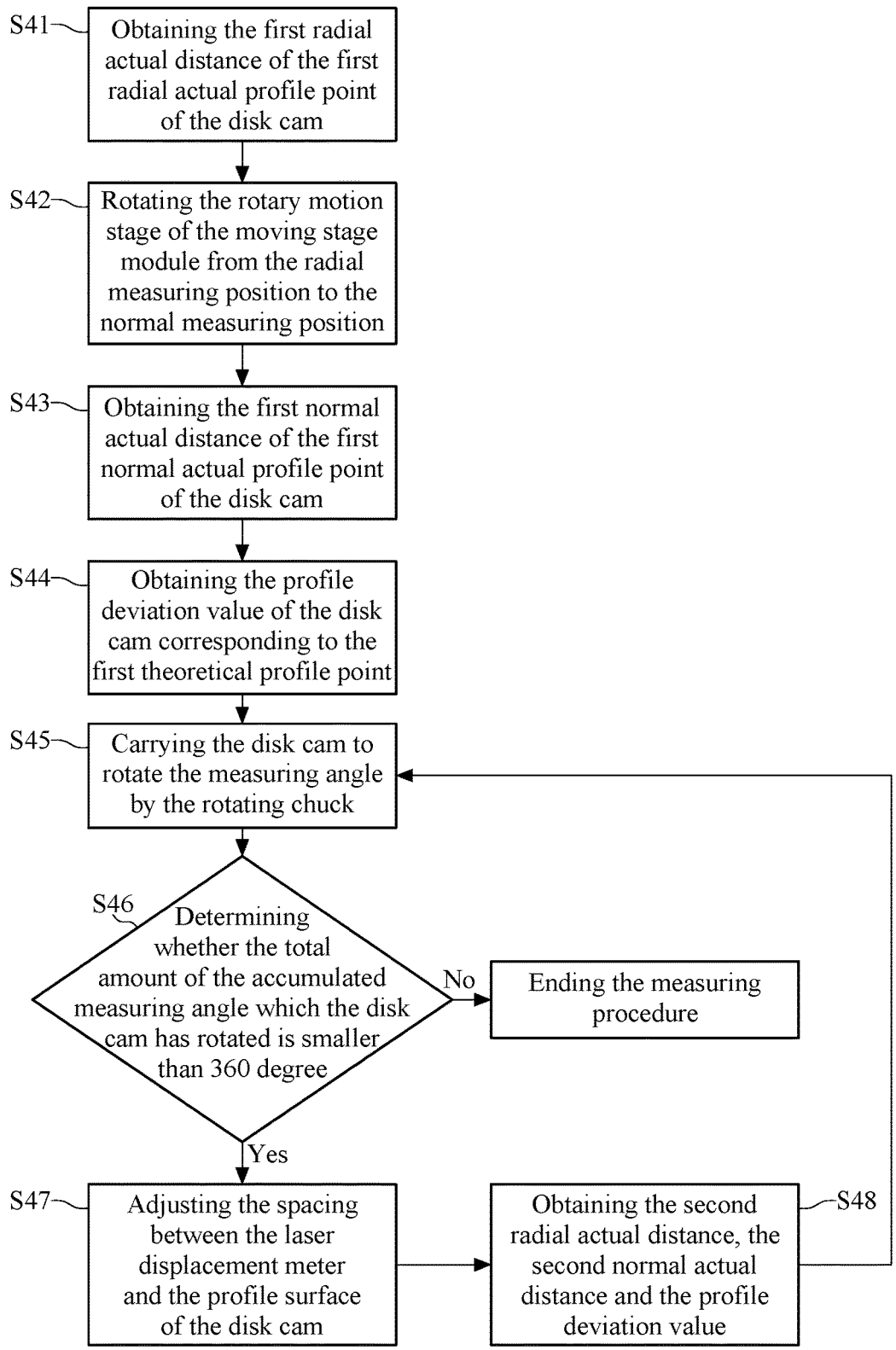
FIG. 4C is a flowchart of the measuring procedure of the optical measuring method in FIG. 4A.
Figure 5A:
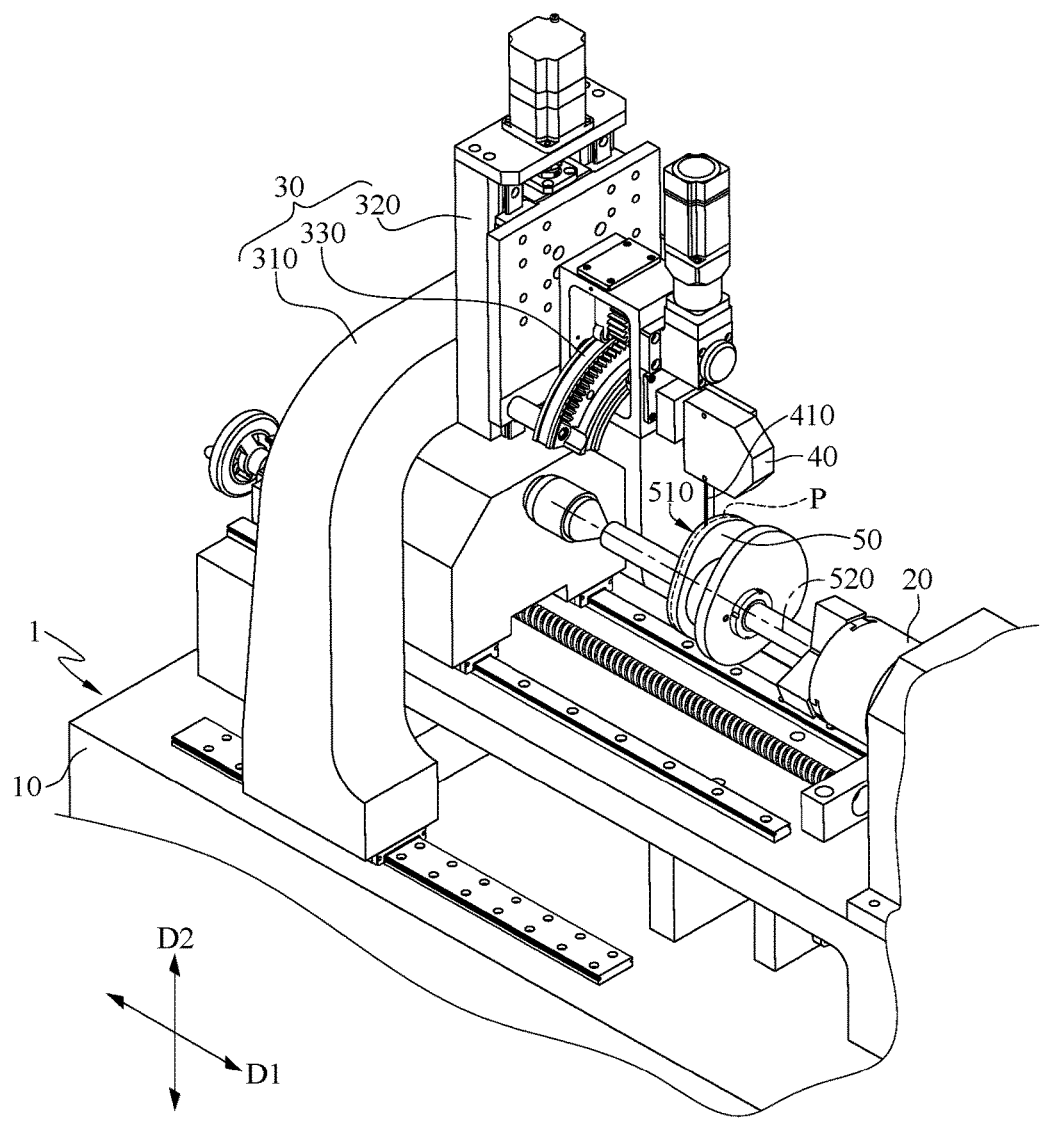
FIG. 5A to FIG. 5G are schematic diagrams of measuring the profile accuracy of a disk cam by the non-contact and optical measuring automation system in FIG. 1A.

The following describes using the non-contact and optical measuring automation system 1 in this embodiment to measure the profile accuracy of a disk cam. Please refer to FIG. 4A to FIG. 5G. FIG. 4A is a flowchart of a non-contact and optical measuring method according to the first embodiment of this disclosure. FIG. 4B is a flowchart of the positioning procedure of the optical measuring method in FIG. 4A. FIG. 4C is a flowchart of the measuring procedure of the optical measuring method in FIG. 4A. FIG. 5A to FIG. 5G are schematic diagrams of measuring the profile accuracy of a disk cam by the non-contact and optical measuring automation system in FIG. 1A. As shown in FIG. 4A, the optical measuring method in this embodiment includes steps S1 to S5. Moreover, as shown in FIG. 5A, before starting the measurement, a disk cam 50 is clamped by the rotating chuck 20 of the non-contact and optical measuring automation system 1.

The disk cam 50 in this embodiment is adapted to a cam mechanism with an offset translating roller follower, but the disclosure is not limited thereto. In some embodiments, the disk cam measure by the non-contact and optical measuring automation system 1 is adapted to a cam mechanism with a translating flat-faced follower or a cam mechanism with an oscillating roller follower, wherein a single disk cam or a conjugate disk cam can be applied in the said cam mechanism.

Firstly, the step S1 is executed. A piece of theoretical profile information of the disk cam 50 is inputted to the computer 2. In this embodiment, the theoretical profile information includes a radius of the base circle of the disk cam 50, a roller radius of the cam mechanism including the disk cam 50, an offset of the roller of the cam mechanism including the disk cam 50, a theoretical thickness of the disk cam 50, specified follower motion equations of the cam mechanism including the disk cam 50, parametric vector equations of the cam profile of the disk cam 50, the coordinates of the cam profile of the disk cam 50, the coordinate of the rotational center of the disk cam 50, pressure angles corresponding to the theoretical cam profile of the disk cam 50, shift angles between radial and normal directions corresponding to the cam profile of the disk cam 50, and so on. The above shift angle between radial and normal directions is defined as the angle subtended between the radial and normal vectors corresponding to the theoretical profile point of the disk cam 50. The magnitude of a shift angle, as that of a conventional pressure angle, varies with the position of different cam profile point (reference source of the definition of a shift angle: Wen-Tung Chang, *Analysis of Mechanical Errors in Planar Cam Mechanisms and Its Applications*, Ph.D. Dissertation, Department of Power Mechanical Engineering, National Tsing Hua University, Hsinchu, Taiwan, 2007, pp. 42-44).

Afterwards, the step S2 is executed. A measuring parameter is set by the computer 2 and includes a cross-section P to be measured, an initial positioning angle α, a measuring angle β, a first theoretical profile point $C_1$ and two second theoretical profile point $C_2$ and $C_2''$ which are selected from the theoretical cam profile 530 of the disk cam 50 and are all different from each other (please refer to FIG. 5C to FIG. 5G). In this embodiment, there are a first radial actual profile point $O_{11}$ and a first normal actual profile point $O_{12}$ which correspond to the first theoretical profile point $C_1$ and have different positions from each other on a profile surface 510 of the disk cam 50. Besides, there is also a second radial actual profile point $O_{21}$ and a second normal actual profile point $O_{22}$ which correspond to the second theoretical profile point $C_2$ and have different positions from each other, and a radial actual profile point (not shown in figures) and a normal actual profile point (not shown in figures) which correspond to the second theoretical profile point $C_2$" and have different positions from each other on the profile surface 510 of the disk cam 50. As shown in FIG. 5A, the cross-section P to be measured is a reference plane located along the axial direction of the disk cam 50, and the cross-section P to be measured is perpendicular to the rotational axis 520 of the disk cam 50. All the first radial actual profile point $O_{11}$, the first normal actual profile point $O_{12}$, the second radial actual profile point $O_{21}$ and the second normal actual profile point $O_{22}$ are located on the cross-section P to be measured. Please refer to FIG. 5C and FIG. 5F, the initial positioning angle α is a rotating angle of the disk cam 50 and whose value is between 0 and 360 degrees. After the rotating chuck 20 rotates the disk cam 50 for the initial positioning angle α, the non-contact and optical measuring automation system 1 executes the measurement for the first radial actual profile point $O_{11}$ and the first normal actual profile point $O_{12}$. After the non-contact and optical measuring automation system 1 completes the measurement for the actual profile point $O_{11}$ and $O_{12}$, the rotating chuck 20 rotates the disk cam 50 for the measuring angle β for executing the measurement for the second radial actual profile point $O_{21}$ and the second normal actual profile point $O_{22}$ by the non-contact and optical measuring automation system 1.

Afterwards, the step S3 is executed. The computer instructs the non-contact and optical measuring automation system 1 to execute a positioning procedure to make the light beam 410 which is emitted from the laser displacement meter 40 align to the cross-section P to be measured and be located at a default standby position before the measurement is executed. As shown in FIG. 4B, in this embodiment, the step S3 includes steps S31 to S33.

As shown in FIG. 5A, the step S31 is executed first. The computer 2 instructs the first linear motion stage 310 of the moving stage module 30 to move relatively to the base 10 in order to carry the second linear motion stage 320, the rotary motion stage 330 and the laser displacement meter 40 to move together along the first direction D1 to the position above the disk cam 50, so that the light beam 410 emitted from the laser displacement meter 40 aligns to the cross-section P to be measured. In this embodiment, the first direction D1 is parallel to the rotational axis 520 of the disk cam 50. Moreover, as shown in FIG. 5C, in this embodiment, the rotary motion stage 330 is located at the radial measuring position before the measurement is executed, so after the step S31 is executed, the travelling direction D3 of the light beam 410 of the laser displacement meter 40 passes through and is perpendicular to the rotational axis 520 of the disk cam 50.

Figure 5B:
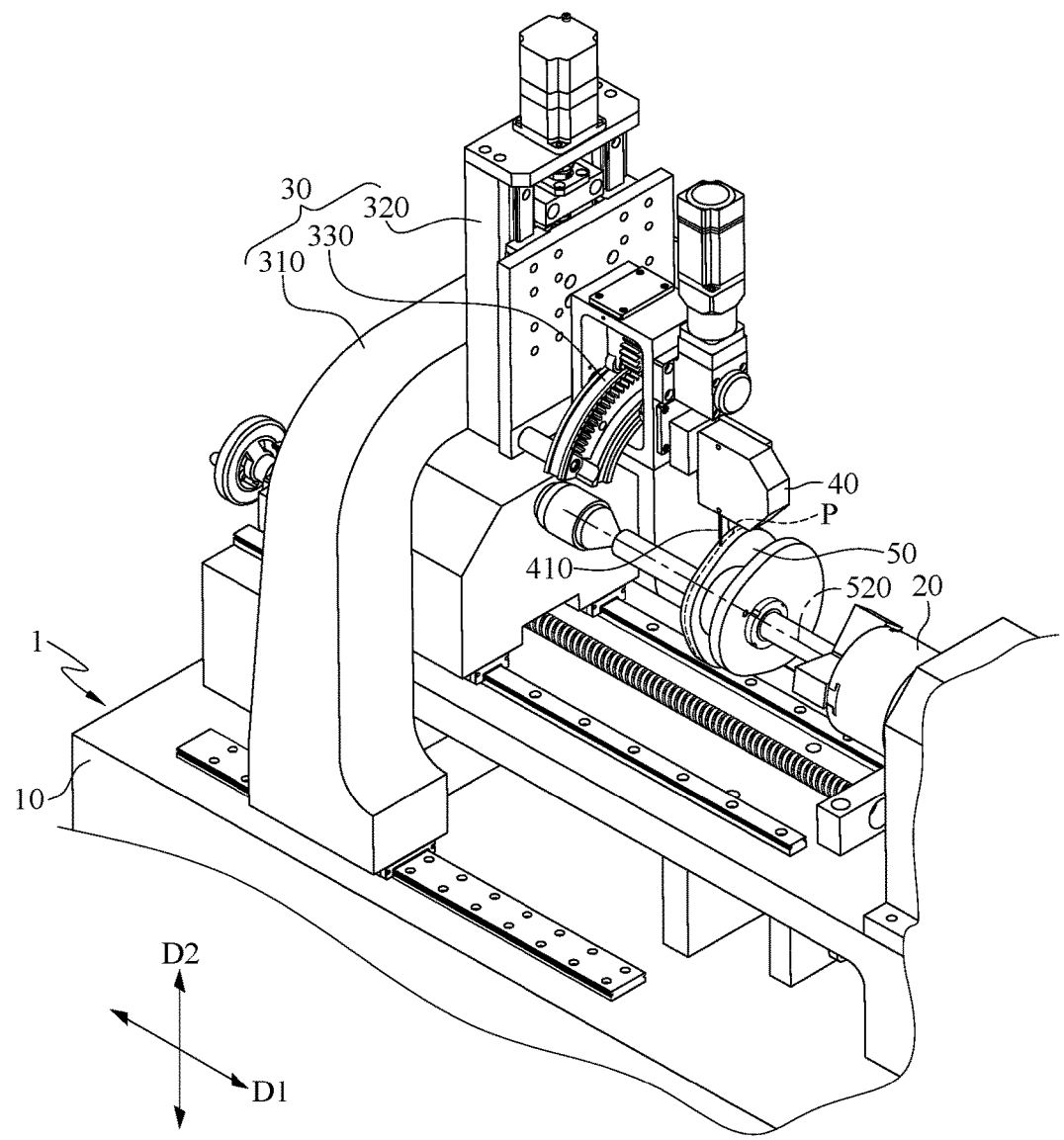
Figure 5C:
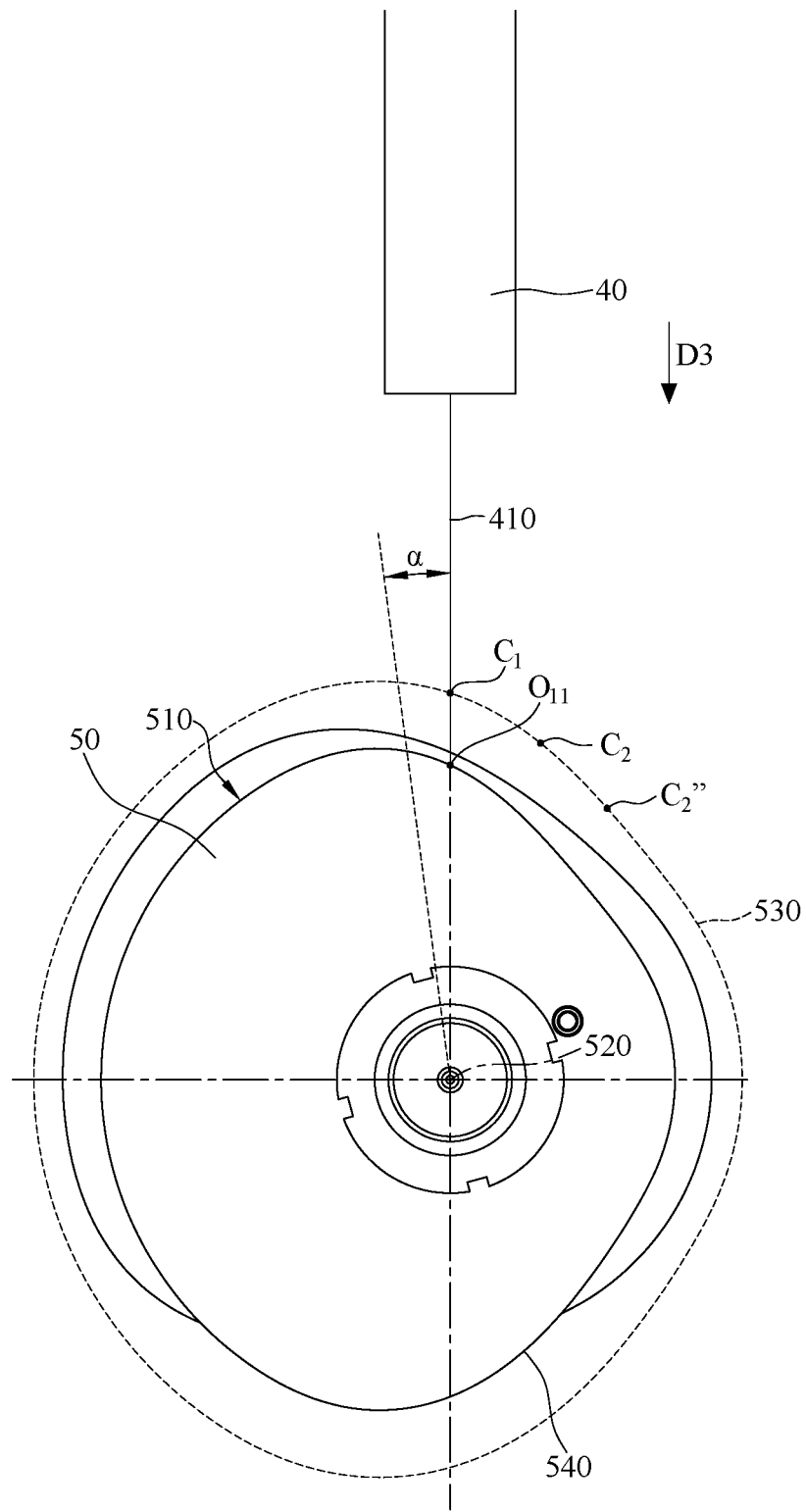

As shown in FIG. 5B and FIG. 5C, the step S32 is then executed. The computer 2 instructs the rotating chuck 20 to rotate the disk cam 50 for the initial positioning angle α so as to aim the light beam 410 which is emitted from the laser displacement meter 40 at the first theoretical profile point $C_1$. In this embodiment, the initial positioning angle α is about 15.22 degrees, but is not limited thereto in this disclosure.

Figure 5D:
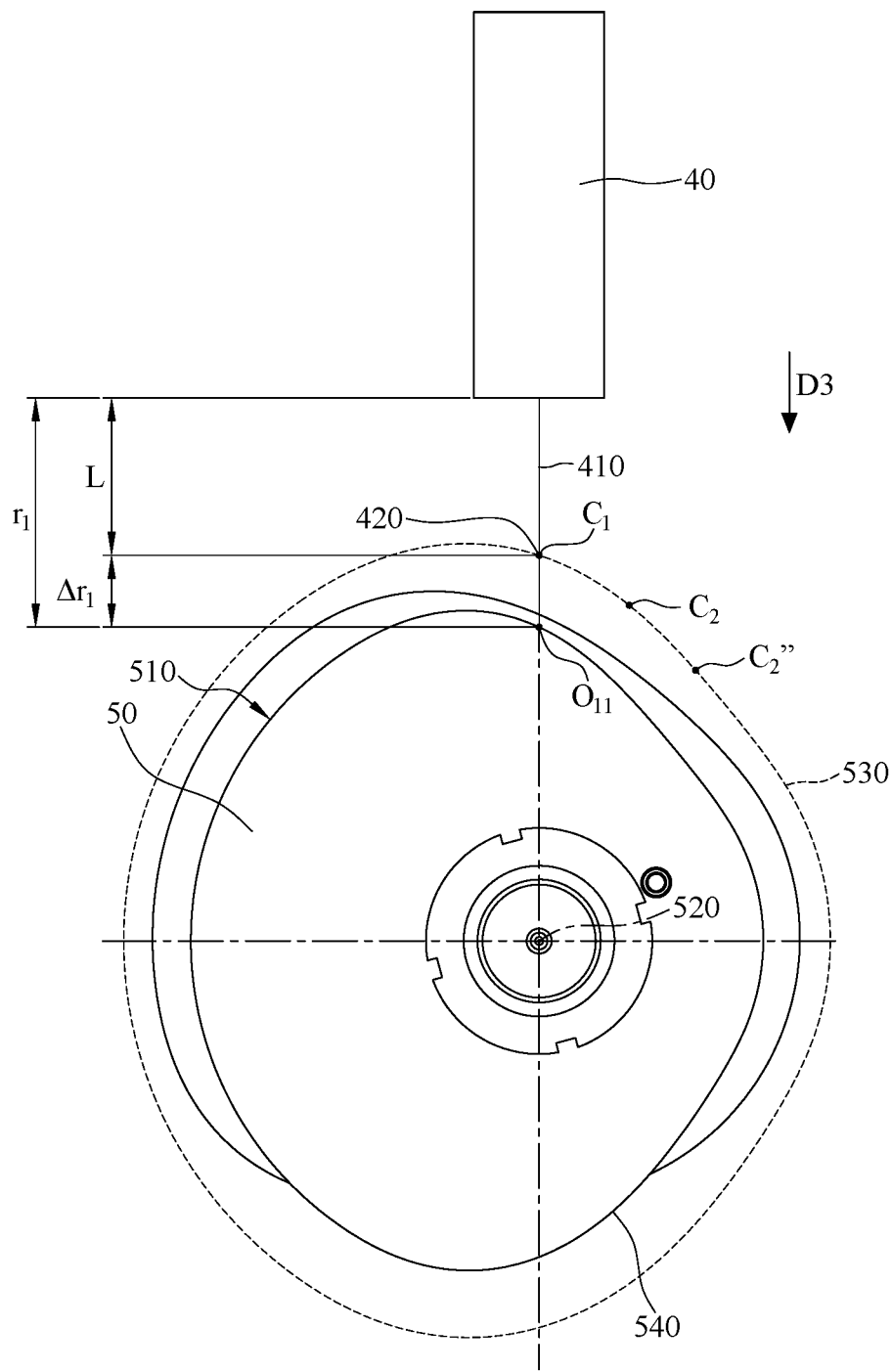

As shown in FIG. 5D, the step S33 is then executed. The computer 2 instructs the second linear motion stage 320 of the moving stage module 30 to move relatively to the first linear motion stage 310 to make both the laser displacement meter 40 and the rotary motion stage 330 close to or far from the disk cam 50 and adjust the spacing between the laser displacement meter 40 and the profile surface 510 of the disk cam 50 so as to locate the measuring datum point 420 of the laser displacement meter 40 at the position of the first theoretical profile point $C_1$. After the step S33 is executed, the measuring datum point 420 of the laser displacement meter 40 overlaps the first theoretical profile point $C_1$ at the theoretical cam profile 530 of the disk cam 50, and at the same time, the spacing between the laser displacement meter 40 and the first theoretical profile point $C_1$ is equal to the theoretical distance L.

In the optical measuring method of this embodiment, the positioning procedure is executed in order from steps S31 to S33, but the executing order of the steps S31, S32 and S33 of this disclosure is not limited to the above.

After the aforementioned positioning procedure is completed, the step S4 is executed. A measuring procedure is executed by the laser displacement meter 40 using a laser triangulation method to obtain the actual distance between the actual profile point of the disk cam 50 and the laser displacement meter 40. More specifically, the actual distance between the disk cam 50 and the laser displacement meter 40, corresponding to the first theoretical profile point $C_1$, comprises a first radial actual distance $r_1$ between the first radial actual profile point $O_{11}$ and the laser displacement meter 40 as well as a first normal actual distance $n_1$ between the first normal actual profile point $O_{12}$ and the laser displacement meter 40. Moreover, the actual distance between the disk cam 50 and the laser displacement meter 40, corresponding to the second theoretical profile point $C_2$, comprises a second radial actual distance $r_2$ between the second radial actual profile point $O_{21}$ and the laser displacement meter 40 as well as a second normal actual distance $n_2$ between the laser displacement meter 40 and the second normal actual profile point $O_{22}$. As shown in FIG. 4C, in this embodiment, the step S4 includes steps S41 to S48. Please refer to the above paragraphs corresponding to FIG. 1B for the laser triangulation method, and the details related to it are not repeated here.

As shown in FIG. 5D, the step S41 is executed first. The computer 2 instructs the laser displacement meter 40 to measure the first radial actual profile point $O_{11}$ (the first measurement). More specifically, the laser displacement meter 40 emits a light beam 410 to the first radial actual profile point $O_{11}$ of the disk cam 50 along the travelling direction D3 so as to obtain the first radial actual distance $r_1$. In this embodiment, the first radial actual distance $r_1$ is a distance between the laser displacement meter 40 and the first radial actual profile point $O_{11}$ along the travelling direction D3.

Figure 5E:
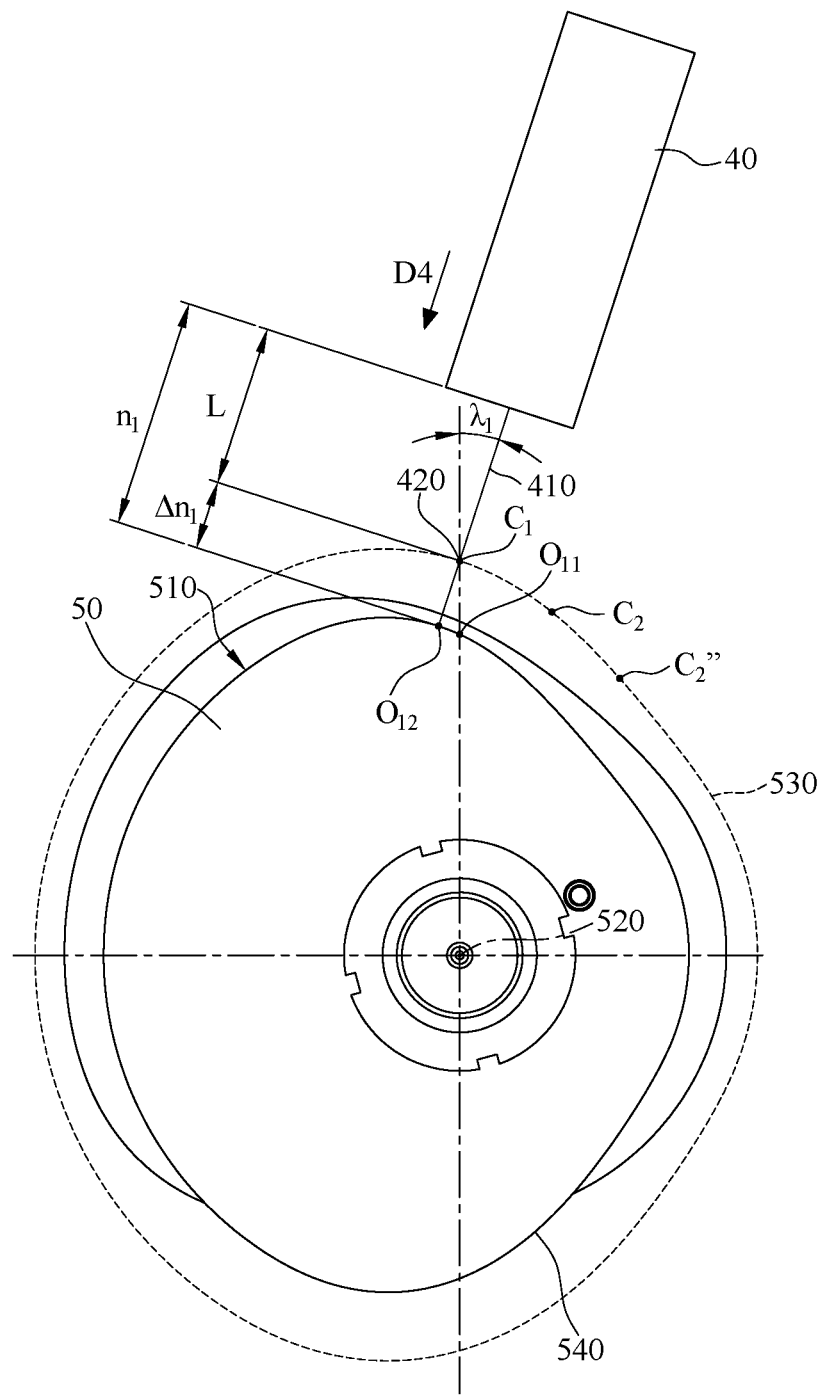

As shown in FIG. 5E, the step S42 is then executed. The computer 2 instructs the rotary motion stage 330 of the moving stage module 30 to rotate a shift angle $\lambda_1$ from the radial measuring position to the normal measuring position, and the shift angle $\lambda_1$ is equal to the shift angle which is subtended between the radial and normal directions and corresponds to the first theoretical profile point $C_1$. When the rotary motion stage 330 is at the normal measuring position, the travelling direction D4 of the light beam 410 is parallel to the normal direction of the profile surface 510 of the disk cam 50 with the normal direction passing through the first theoretical profile point $C_1$.

If the measuring datum point 420 of the laser displacement meter 40 deviates from the theoretical cam profile 530 of the disk cam 50 as the step S42 executed, the computer can instruct the second linear motion stage 320 to adjust the position of the laser displacement meter 40 so that the measuring datum point 420 and the first theoretical profile point $C_1$ overlap each other, and at the same time, the spacing between the laser displacement meter 40 and the first theoretical profile point $C_1$ is equal to the theoretical distance L.

Afterwards, the step S43 is executed. The computer 2 instructs the laser displacement meter 40 to measure the first normal actual profile point $O_{12}$ (the first measurement). More specifically, the laser displacement meter 40 emits a light beam 410 to the first normal actual profile point $O_{12}$ of the disk cam 50 along the travelling direction D4 so as to obtain the first normal actual distance $n_1$. In this embodiment, the first normal actual distance $n_1$ is a distance between the laser displacement meter 40 and the first normal actual profile point $O_{12}$ along the travelling direction D4. The rotary motion stage 330 returns to the radial measuring position after obtaining the first normal actual distance $n_1$.

The step S44 is then executed. The computer 2 calculates the difference values between the theoretical distance L and the first radial actual distance $r_1$ and between the theoretical distance L and the first normal actual distance $n_1$ according to the theoretical distance L which is obtained by inputting the theoretical cam profile 530 of the disk cam 50 in the step S1 and said two actual distance $r_1$ and $n_1$ which are obtained in the step S4, so as to obtain a profile deviation value of the disk cam 50 corresponding to the first theoretical profile point $C_1$. The profile deviation value is the first radial profile deviation value $\Delta r_1$ ($\Delta r_1 = L - r_1$) or the first normal profile deviation value $\Delta n_1$ ($\Delta n_1 = L - n_1$). More specifically, after the theoretical profile information of the disk cam 50 is inputted in the step S1, the theoretical distance L between the laser displacement meter 40 and the first theoretical profile point $C_1$ is obtained. The measuring datum point 420 of the laser displacement meter 40 overlaps the first theoretical profile point $C_1$ after the steps S33 and S42 are executed, so that when the actual cam profile 540 of the disk cam 50 is identical to the theoretical cam profile 530 (i.e. the actual distance is equal to the theoretical distance), the profile deviation value, which is obtained by inputting the distance between the profile surface 510 and the laser displacement meter 40 measured by the laser displacement meter 40 to the computer 2, is zero.

As shown in FIG. 5D and FIG. 5E, when the distance between the first radial actual profile point $O_{11}$ of the disk cam 50 and the laser displacement meter 40 or the distance between the first normal actual profile point $O_{12}$ and the laser displacement meter 40 is larger than the theoretical distance L, the first radial profile deviation value $\Delta r_1$ or the first normal profile deviation value $\Delta n_1$ obtained during the measuring procedure is negative, which means the dimension of the actual cam profile 540 of the disk cam 50 is smaller than that of the theoretical cam profile 530; that is, the profile deviation value of the disk cam 50 corresponding to the first theoretical profile point $C_1$ is negative. On the contrary, when the distance between the first radial actual profile point $O_{11}$ and the laser displacement meter 40 or the distance between the first normal actual profile point $O_{12}$ and the laser displacement meter 40 is smaller than the theoretical distance L, the first radial profile deviation value $\Delta r_1$ or the first normal profile deviation value $\Delta n_1$ obtained during the measuring procedure is positive, which means the dimension of the actual cam profile 540 of the disk cam 50 is larger than that of the theoretical cam profile 530; that is, the profile deviation value of the disk cam 50 corresponding to the first theoretical profile point $C_1$ is positive.

Figure 5F:
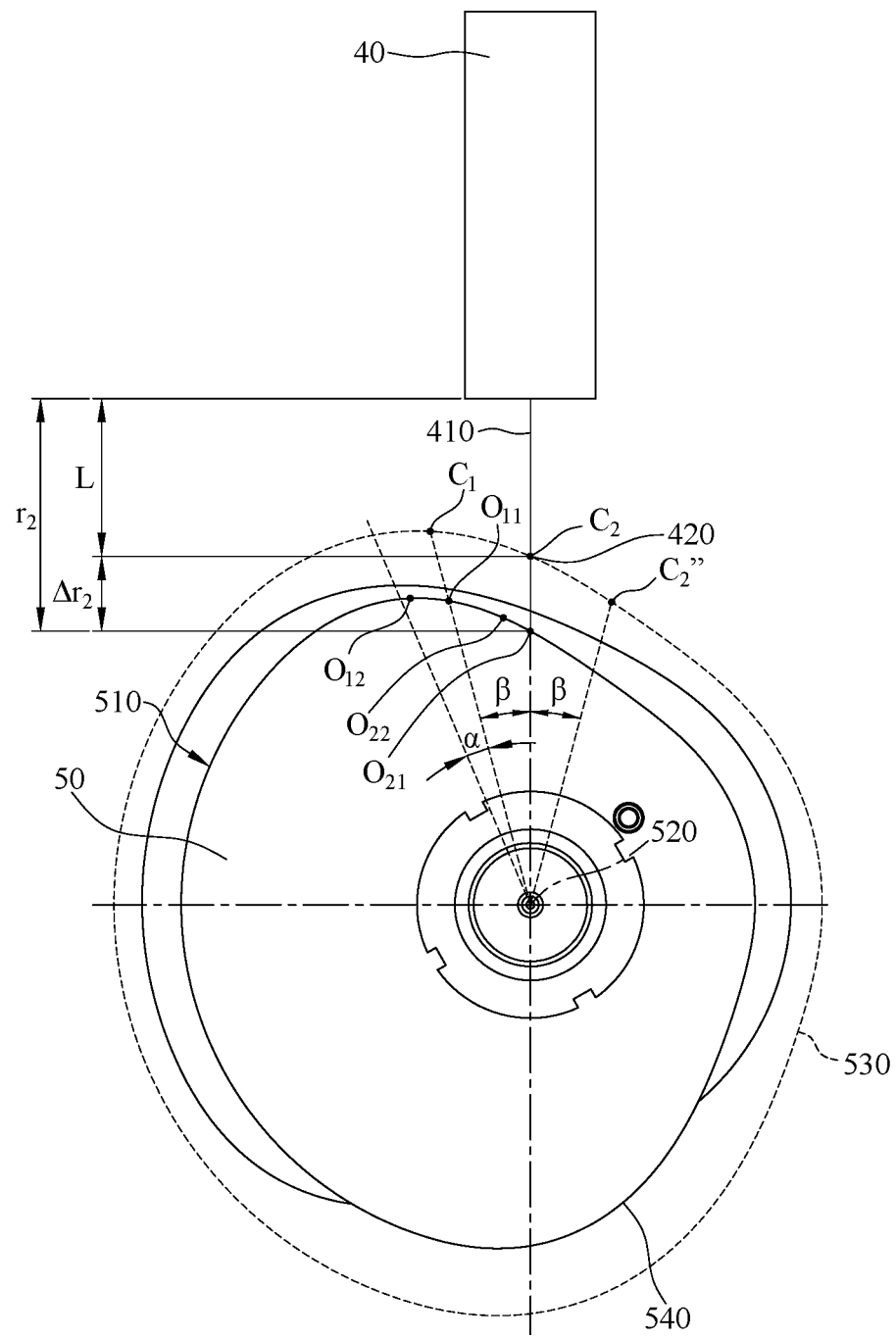
Figure 5G:
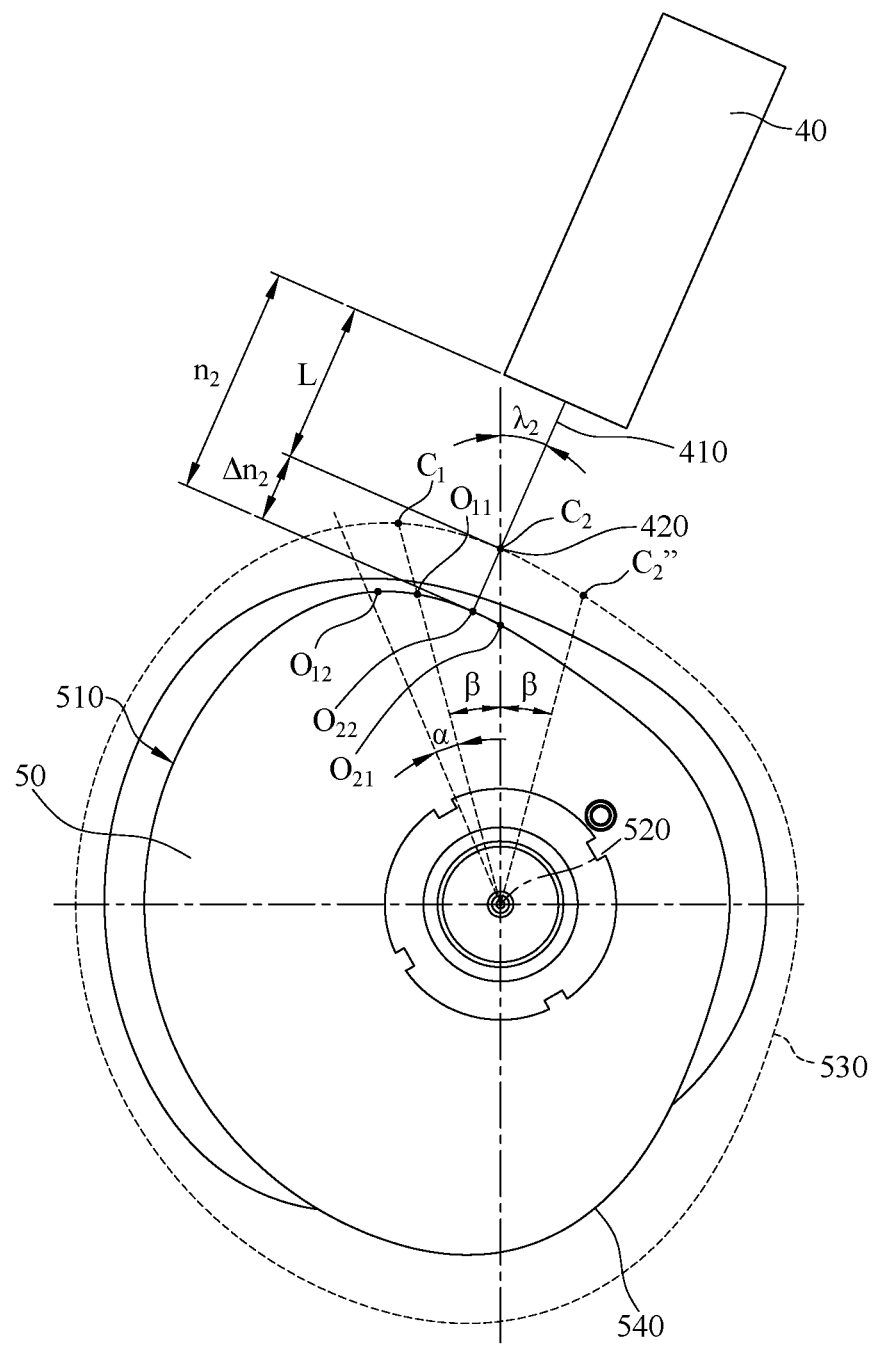

As shown in FIG. 5F and FIG. 5G, after the measuring procedure is completed and the first radial actual distance $r_1$ and the first normal actual distance $n_1$ are obtained, the step S45 is executed. The computer 2 instructs the rotating chuck 20 to carry the disk cam 50 to rotate a measuring angle β so that the light beam 410 of the laser displacement meter 40 aims at the second theoretical profile point $C_2$. In this embodiment, the measuring angle β is about 30 degrees, but is not limited thereto.

Afterwards, the step S46 is executed. The computer 2 determines whether the total amount of an accumulated measuring angle which the disk cam 50 has rotated is smaller than 360 degrees, and ends the measuring procedure second theoretical profile point $C_2$ if the determination result is negative, or continuously executes the measuring procedure for the second theoretical profile point $C_2$ if the determination result is positive. In this embodiment, when the laser displacement meter 40 aims at the second theoretical profile point $C_2$, the total amount of the accumulated measuring angle, 1β is about 30 degrees, so that the determination result is positive in the step S46 and the laser displacement meter 40 is instructed to measure the second radial actual profile point $O_{21}$ and the second normal actual profile point $O_{22}$ (the second measurement).

When the determination result is negative in the step S46, the step S47 is then executed to adjust the spacing between the laser displacement meter 40 and the profile surface 510 of the disk cam 50 to locate the measuring datum point 420 of the laser displacement meter 40 at the second theoretical profile point $C_2$. More specifically, after the rotating chuck 20 rotates the disk cam 50, the measuring datum point 420 of the laser displacement meter 40 deviates from the theoretical cam profile 530 of the disk cam 50, so the position of the laser displacement meter 40 has to be adjusted to make the measuring datum point 420 overlap the second theoretical profile point $C_2$ of the theoretical cam profile 530. In other words, as shown in FIG. 5D and FIG. 5F, the spacing (i.e. theoretical distance L) between the laser displacement meter 40 and the first theoretical profile point $C_1$ in the step S41 is equal to the spacing (i.e. theoretical distance L) between the laser displacement meter 40 and the second theoretical profile point $C_2$ in the step S47. Thereby, the sign of the measured radial profile deviation value as well as the measured normal profile deviation value directly indicates whether the actual cam profile 540 of the disk cam 50 is larger or smaller than the theoretical cam profile 530, and the difference value (a theoretical offset distance) between the theoretical profile point and the measuring datum point 420 of the laser displacement meter 40 is not involved in the measurement, so that it may simplify the measuring method and enhance measuring efficiency.

In the optical measuring method of this embodiment, the step S47 is executed after the step S46, but the executing order of the steps S46 and S47 of this disclosure is not limited thereto.

After the step S47 is executed, the step S48 is then executed. The measurement is executed by the laser displacement meter 40 to obtain the second radial actual distance $r_2$ between the second radial actual profile point $O_{21}$ and the laser displacement meter 40 as well as the second normal actual distance $n_2$ between the second normal actual profile point $O_{22}$ and the laser displacement meter 40. As shown in FIG. 5F, the rotary motion stage 330 is located at the radial measuring position as measuring the second radial actual distance $r_2$; as shown in FIG. 5G, the rotary motion stage 330 rotates a shift angle $\lambda_2$ from the radial measuring position to the normal measuring position, and than measures the second normal actual distance $n_2$. The shift angle $\lambda_2$ is equal to the shift angle of the disk cam 50, with the shift angle subtended between radial and normal directions and corresponding to the second theoretical profile point $C_2$. After the step of measuring the second normal actual distance $n_2$, the rotary motion stage 330 returns to the radial measuring position. The computer 2 then calculates the difference value between the theoretical distance L and the second radial actual distance $r_2$ as well as the difference value between the theoretical distance L and the second normal actual distance $n_2$ according to these three distances so as to obtain the profile deviation value of the disk cam 50 corresponding to the second theoretical profile point $C_2$ wherein the profile deviation value is the second radial profile deviation value $\Delta r_2$ ($\Delta r_2 = L - r_2$) or the second normal profile deviation value $\Delta n_2$ ($\Delta n_2 = L - n_2$). In this embodiment, the laser displacement meter 40 executes the measurement for each theoretical profile point by the same measuring method, so that the specific details of the step S48 is similar to the aforementioned steps S41 to S44 and not described again.

After obtaining the second radial actual distance $r_2$ and the second normal actual distance $n_2$, the computer 2 instructs the rotating chuck 20 to carry the disk cam 50 to rotate the measuring angle β again, so that the light beam 410 of the laser displacement meter 40 aims at another second theoretical profile point $C_2$". Afterwards, the computer 2 executes the step S46 again so as to determine whether the total amount of the accumulated measuring angle, which the disk cam 50 has rotated, is less than 360 degrees. In this embodiment, when the laser displacement meter 40 aims at the second theoretical profile point $C_2$", the total amount of the accumulated measuring angle, 2β, which the disk cam 50 has rotated is 60 degrees, so that the determination result of the step S46 is still positive and the measuring procedure for the actual profile point corresponding to the second theoretical profile point $C_2$" is then executed (the third measurement).

In this embodiment, when the measuring procedure was executed twelve times (i.e. the disk cam 50 has rotated the measuring angle β for eleven times) and then the disk cam 50 rotates the measuring angle β again, the total amount of the accumulated measuring angle, 12β, which the disk cam 50 has rotated is about 360 degrees, so that the computer 2 determines the total amount of the accumulated measuring angle 12β is not less than 360 degrees and then ends the measuring procedure.

When the determination result of the step S46 is negative, the measuring procedure is ended and the step S5 is executed. The measured radial actual distance, normal actual distance, profile deviation value etc. are respectively outputted and displayed on the human-machine interface 22 of the computer 2 for a user to conduct further data statistic and analysis.

In this embodiment, during the measurement, the measuring datum point 420 of the laser displacement meter 40 overlaps the theoretical profile point of the theoretical cam profile 530 corresponding to the actual profile point being measured, but this disclosure is not limited to it. In another embodiment, the measuring datum point 420 of the laser displacement meter 40 does not overlap the theoretical profile point but has a theoretical offset distance from the theoretical profile point. In this case, the computer 2 or the user further calculates the difference value between the actual distance and the theoretical offset distance after obtaining the radial actual distance and the normal actual distance, so as to obtain the profile deviation value between the actual profile point of the disk cam 50 and the theoretical profile point.

Moreover, in this embodiment, the radial actual distance $r_1$, $r_2$, and the normal actual distance $n_1$, $n_2$ measured by the laser displacement meter 40 are the distances between the profile surface 510 of the disk cam 50 and the laser displacement meter 40, but this disclosure is not limited thereto. In another embodiment, the radial actual distances and the normal actual distances measured by the laser displacement meter 40 indicate the coordinates of the actual profile points of the actual cam profile 540 of the disk cam 50, and the computer 2 or the user can further calculate the distances between the coordinates of the actual cam profile 540 and those of the theoretical cam profile 530 so as to obtain the profile deviation values of the disk cam 50.

In addition, in the measuring procedure of this embodiment, the non-contact and optical measuring automation system 1 totally measures twelve actual profile points and obtains twelve radial actual distances and twelve normal actual distances, but the amount of the actual profile points in this disclosure is not limited to it.

Besides, in the measuring procedure of this embodiment, the computer 2 instructs the laser displacement meter 40 to measure the radial actual distance and the normal actual distance corresponding to a theoretical profile point when measuring the profile deviation for the same theoretical profile point, but this disclosure is not limited to it. In another embodiment, the computer 2 instructs the laser displacement meter 40 to merely measure the radial actual distance or the normal actual distance.

Furthermore, in the optical measuring method of this embodiment, the position of the theoretical profile point to be measured is determined through setting the initial positioning angle α and the measuring angle β, but this disclosure is not limited to it. In another embodiment, during the setting of the measuring parameter, a plurality of coordinates in the theoretical cam profile 530 of the disk cam 50 can be selected directly as the theoretical profile points to be measured.

Figure 6:
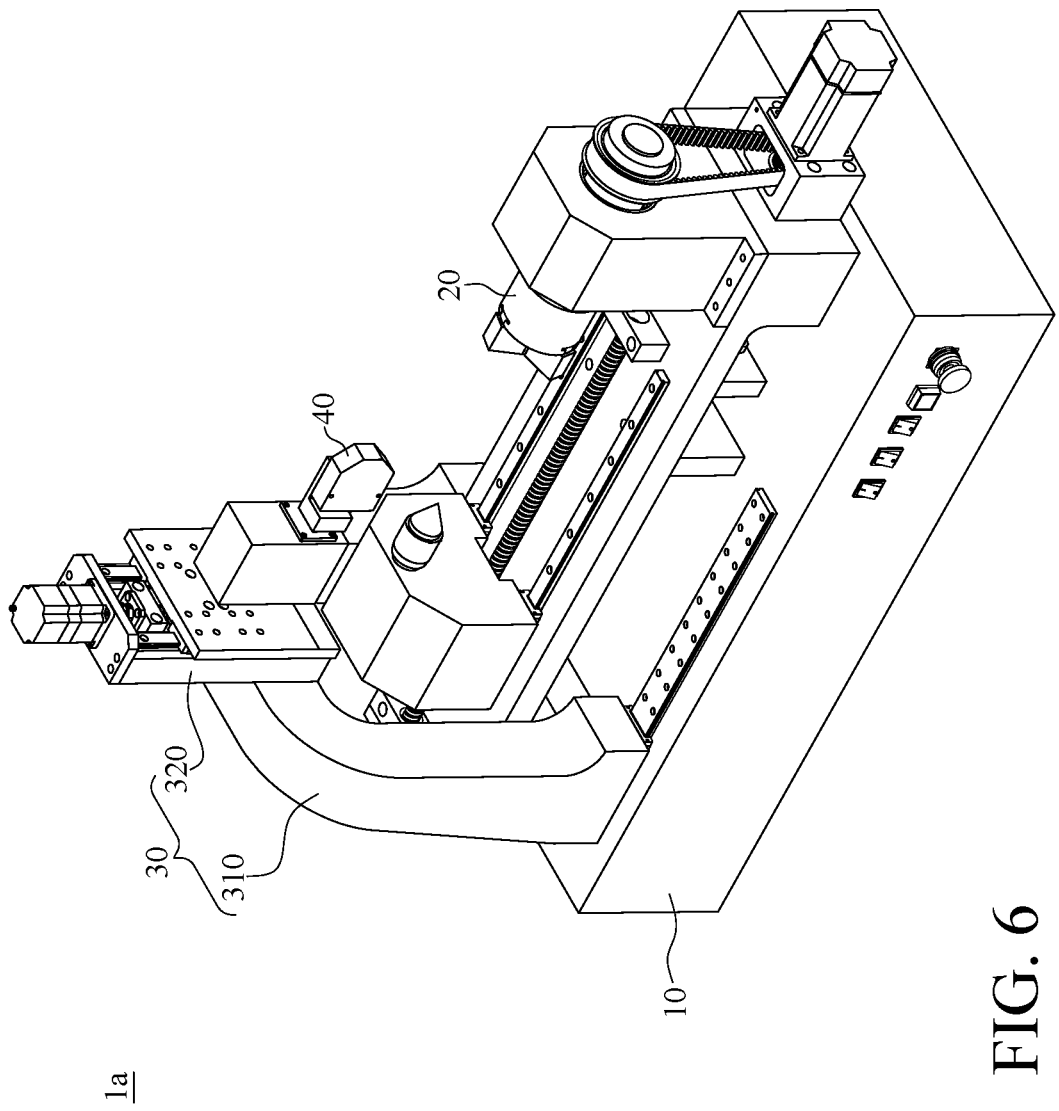
FIG. 6 is a perspective view of a non-contact and optical measuring automation system according to the second embodiment of this disclosure.
Figure 7:
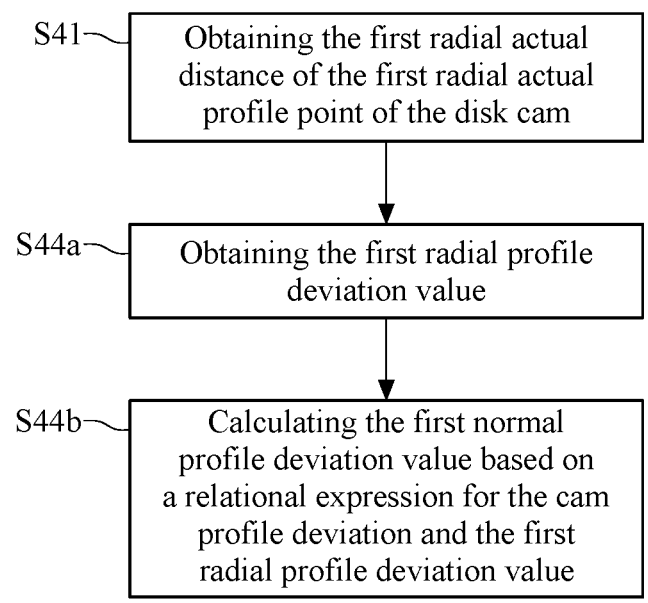
FIG. 7 is a flowchart of a part of the measuring procedure of a non-contact and optical measuring method according to the second embodiment of this disclosure.

In the first embodiment, the rotary motion stage 330 of the moving stage module 30 can carry the laser displacement meter 40 to rotate together, so that the laser displacement meter 40 can measure the radial actual distance and the normal actual distance of the disk cam 50 in sequence, but the disclosure is not limited to it. FIG. 6 is a perspective view of a non-contact and optical measuring automation system according to the second embodiment of this disclosure. FIG. 7 is a flowchart of a part of the measuring procedure of a non-contact and optical measuring method according to the second embodiment of this disclosure. Because the second embodiment is similar to the first embodiment, merely the difference between these two embodiments is explained in the following.

The second embodiment provides a non-contact and optical measuring automation system 1a. The moving stage module 30 of the non-contact and optical measuring automation system 1a comprises a first linear motion stage 310 and a second linear motion stage 320 but does not comprise a rotary motion stage.

As shown in FIG. 7, in the non-contact and optical measuring method of the second embodiment, after the step S41 is completed, the step S44a is directly executed without the steps S42 and S43 described in the first embodiment, so as to obtain the first radial profile deviation value, and then the step S44b is executed. In the step S44b, the computer 2 can conduct calculation based on a relational expression for the cam profile deviation and the first radial profile deviation value measured in the step S44a, so as to obtain an approximate solution of the first normal profile deviation value with sufficient accuracy. The said relational expression for the cam profile deviation is: $\Delta n_1 \approx \Delta r_1 \times \cos \lambda_1$ (reference of the relational expression for the cam profile deviation: Wen-Tung Chang, *Analysis of Mechanical Errors in Planar Cam Mechanisms and Its Applications*, Ph.D. Dissertation, Department of Power Mechanical Engineering, National Tsing Hua University, Hsinchu, Taiwan, 2007, pp. 42-44). Wherein $\Delta r_1$ represents the first radial profile deviation value, $\Delta n_1$ represents the first normal profile deviation value and $\lambda_1$ represents the shift angle between the radial and normal directions as the disk cam 50 measured for the first theoretical profile point $C_1$ (i.e. the shift angle $\lambda_1$ described in the step S42 of the first embodiment). Similarly, the computer 2 can conduct calculation based on the relational expression for the cam profile deviation and the measured second radial profile deviation value so as to obtain the second normal profile deviation value, wherein the relational expression is: $\Delta n_2 \approx \Delta r_2 \times \cos \lambda_2$ (please refer to the description of the step S48 of the first embodiment for the meaning of each symbol in the relational expression).

The disposition of the rotary motion stage 330 in the first embodiment might increase the hardware cost of the measuring system. Therefore, in the optical measuring method of the second embodiment, the radial profile deviation value obtained by the laser displacement meter 40 is substituted into the relational expression for the cam profile deviation to obtain the normal profile deviation value. Thereby, part of the hardware cost may be reduced. Also, the laser displacement meter 40 does not have to rotate from the radial measuring position to the normal measuring position, so that the measurement efficiency may be enhanced.

In view of the above description, the non-contact and optical measuring automation system and the non-contact and optical measuring method of this disclosure measure the actual distance of a disk cam by a laser displacement meter, and then obtain the profile deviation value of the disk cam based on the difference value between the theoretical distance and actual distance of the disk cam. Thereby, when the disk cam has the geometric feature of concave profile, the laser displacement meter can measure the profile deviation value of the hollow part of the concave profile of the disk cam since the light beam emitted from the laser displacement meter will not be blocked by another part of the profile. Therefore, the non-contact and optical measuring automation system and the non-contact and optical measuring method of this disclosure are applied to a disk cam with the geometric feature of convex profile as well as that with the geometric feature of concave profile, and is conducive to improve the drawback that the conventional non-contact measuring device and method, such as a laser scanner or an optical micrometer, are limited by the geometric form of a cam profile. Moreover, the non-contact and optical measuring automation system and method of this disclosure may totally replace the conventional contact measuring device and method in function.

What is claimed is:

1. A non-contact and optical measuring automation system, configured to electrically connect to a computer to measure a profile accuracy of a disk cam, and the non-contact and optical measuring automation system comprising:
    a base;
    a rotating chuck, disposed on the base and configured to clamp the disk cam to allow the disk cam to rotate around a rotational axis of the disk cam;
    a moving stage module, comprising a first linear motion stage and a second linear motion stage, with the first linear motion stage disposed on the base and movable relatively to the base in a first direction, and with the second linear motion stage disposed on the first linear motion stage and movable relatively to the first linear motion stage in a second direction non-parallel to the first direction so as to be close to or far from the disk cam; and
    a laser displacement meter, disposed on the second linear motion stage, and the second linear motion stage being configured to carry the laser displacement meter to move together in the second direction;
    wherein theoretical profile information of the disk cam comprises a theoretical profile point, a theoretical distance between the theoretical profile point and the laser displacement meter is defined, a profile surface of the disk cam comprises an actual profile point corresponding to the theoretical profile point, the computer is configured to instruct the rotating chuck to carry the disk cam to rotate and is configured to instruct the moving stage module to carry the laser displacement meter to move, the computer is further configured to instruct a light beam emitted from the laser displacement meter to project onto the actual profile point and then to obtain an actual distance between the actual profile point of the disk cam and the laser displacement meter by a laser triangulation method, and the computer obtains a profile deviation value of the disk cam corresponding to the theoretical profile point according to a difference value between the actual distance and the theoretical distance.

2. The non-contact and optical measuring automation system according to claim 1, wherein the first direction is parallel to the rotational axis of the disk cam, and the second direction is perpendicular to the first direction.

3. The non-contact and optical measuring automation system according to claim 1, wherein a travelling direction of the light beam emitted from the laser displacement meter passes through and is perpendicular to the rotational axis of the disk cam.

4. The non-contact and optical measuring automation system according to claim 1, wherein the moving stage module further comprises a rotary motion stage, the rotary motion stage is rotatably disposed on the second linear motion stage, and the laser displacement meter is disposed on the rotary motion stage, the rotary motion stage is configured to carry the laser displacement meter to rotate together relatively to the second linear motion stage so as to make a travelling direction of the light beam emitted from the laser displacement meter be parallel to a normal direction of the profile surface of the disk cam corresponding to the theoretical profile point.

5. The non-contact and optical measuring automation system according to claim 1, wherein the moving stage module further comprises a rotary motion stage, the rotary motion stage is rotatably disposed on the second linear motion stage and has a radial measuring position and a normal measuring position, and the laser displacement meter is disposed on the rotary motion stage;

wherein the actual profile point comprises a radial actual profile point and a normal actual profile point which are different from each other, the actual distance comprises a radial actual distance between the radial actual profile point and the laser displacement meter as well as a normal actual distance between the normal actual profile point and the laser displacement meter, the light beam emitted from the laser displacement meter projects onto the radial actual profile point of the disk cam along a direction passing through the rotational axis of the disk cam to obtain the radial actual distance when the rotary motion stage is at the radial measuring position, the light beam projects onto the normal actual profile point along a normal direction of the profile surface corresponding to the theoretical profile point to obtain the normal actual distance when the rotary motion stage is at the normal measuring position, and the computer obtains the profile deviation value of the theoretical profile point according to a difference value between the theoretical distance and at least one of the radial actual distance and the normal actual distance.

6. A non-contact and optical measuring method for measuring a profile accuracy of a disk cam, and the non-contact and optical measuring method comprising:
inputting theoretical profile information of the disk cam;
setting a measuring parameter, with the measuring parameter comprising at least one theoretical profile point of the theoretical profile information, with a theoretical distance defined between the at least one theoretical profile point and a laser displacement meter, and with the at least one theoretical profile point corresponding to at least one actual profile point of a profile surface of the disk cam; and
executing a measuring procedure by the laser displacement meter, making a light beam emitted from the laser displacement meter project onto the at least one actual profile point so as to obtain an actual distance of the at least one actual profile point of the disk cam by a laser triangulation method, and obtaining a profile deviation value of the disk cam corresponding to the at least one theoretical profile point according to a difference value between the theoretical distance and the actual distance.

7. The non-contact and optical measuring method according to claim 6, further comprising executing a positioning procedure, with the measuring parameter further comprising a cross-section to be measured located along an axial direction of the disk cam, the at least one actual profile point located on the cross-section to be measured, and the positioning procedure comprising:
moving the laser displacement meter to make the light beam emitted from the laser displacement meter align to the cross-section to be measured; and
adjusting a spacing between the laser displacement meter and the profile surface of the disk cam to make a measuring datum point of the laser displacement meter overlap the at least one theoretical profile point.

8. The non-contact and optical measuring method according to claim 6, wherein the at least one actual profile point comprises a radial actual profile point and a normal actual profile point which are different from each other, the actual distance comprises a radial actual distance between the radial actual profile point and the laser displacement meter as well as a normal actual distance between the normal actual profile point and the laser displacement meter, and the measuring procedure comprises:
obtaining the radial actual distance by the laser displacement meter;
rotating the laser displacement meter to make a travelling direction of the light beam be parallel to a normal direction of the profile surface of the disk cam corresponding to the at least one theoretical profile point;
obtaining the normal actual distance by the laser displacement meter; and
obtaining the profile deviation value of the disk cam corresponding to the at least one theoretical profile point according to a difference value between the theoretical distance and the radial actual distance or between the theoretical distance and the normal actual distance.

9. The non-contact and optical measuring method according to claim 6, wherein the at least one theoretical profile point comprises a first theoretical profile point and at least one second theoretical profile point which are different from each other, the at least one actual profile point comprises a first actual profile point and at least one second actual profile point which are different from each other, the first theoretical profile point corresponds to the first actual profile point, the at least one second theoretical profile point corresponds to the at least one second actual profile point, and the measuring procedure comprises:
obtaining a first actual distance between the first actual profile point and the laser displacement meter by the laser displacement meter, and obtaining a first profile deviation value of the disk cam corresponding to the first theoretical profile point according to a difference value between the theoretical distance and the first actual distance;
rotating the disk cam for at least one measuring angle to make the laser displacement meter aim at the at least one second theoretical profile point;
obtaining a second actual distance between the at least one second actual profile point and the at least one second actual profile point by the laser displacement meter, and obtaining a second profile deviation value of the disk cam corresponding to the at least one second theoretical profile point according to a difference value between the theoretical distance and the second actual distance; and
determining whether a total amount of an accumulated measuring angle is less than 360 degrees to obtain a determination result, and ending the measuring procedure if the determination result is negative, or continuously executing the measuring procedure if the determination result is positive.

10. The non-contact and optical measuring method according to claim 9, wherein a spacing between the laser displacement meter and the first theoretical profile point is equal to a spacing between the laser displacement meter and the at least one second theoretical profile point.

* * * * *